(12) United States Patent
Mikkelsen et al.

(10) Patent No.: US 9,321,748 B2
(45) Date of Patent: Apr. 26, 2016

(54) AMINOPYRIDINE DERIVED COMPOUNDS AS LRRK2 INHIBITORS

(71) Applicants: H. Lundbeck A/S, Valby (DK); Vernalis (R&D) Ltd., Winnersh (GB)

(72) Inventors: Gitte Kobberøe Mikkelsen, Ballerup (DK); Laurent David, Malmö (SE); Stephen Watson, Hertfordshire (GB); Garrick Paul Smith, Valby (DK); Douglas Stewart Williamson, Winnersh (GB); I-Jen Chen, Winnersh (GB)

(73) Assignees: H. Lundbeck A/S, Valby (DK); Vernalis (R&D) Ltd., Winnersh (GB)

( * ) Notice: Subject to any disclaimer, the term of this patent is extended or adjusted under 35 U.S.C. 154(b) by 0 days.

(21) Appl. No.: 14/758,884

(22) PCT Filed: Dec. 30, 2013

(86) PCT No.: PCT/EP2013/078105
§ 371 (c)(1),
(2) Date: Jul. 1, 2015

(87) PCT Pub. No.: WO2014/106612
PCT Pub. Date: Jul. 10, 2014

(65) Prior Publication Data
US 2015/0336942 A1    Nov. 26, 2015

Related U.S. Application Data

(60) Provisional application No. 61/777,120, filed on Mar. 12, 2013, provisional application No. 61/748,142, filed on Jan. 2, 2013.

(30) Foreign Application Priority Data

Jan. 2, 2013 (DK) ................................. 2013 00004
Mar. 11, 2013 (DK) ................................. 2013 00136

(51) Int. Cl.
C07D 401/04     (2006.01)
C07D 401/14     (2006.01)
C07D 403/14     (2006.01)
C07D 413/04     (2006.01)
C07D 413/14     (2006.01)

(52) U.S. Cl.
CPC ............ *C07D 401/14* (2013.01); *C07D 401/04* (2013.01); *C07D 403/14* (2013.01); *C07D 413/04* (2013.01); *C07D 413/14* (2013.01)

(58) Field of Classification Search
CPC .. C07D 401/04; C07D 401/14; C07D 403/14; C07D 413/04; C07D 413/14
See application file for complete search history.

(56) References Cited

FOREIGN PATENT DOCUMENTS

| WO | 03/093297 A2 | 11/2003 |
| WO | 2007/111904 A2 | 10/2007 |
| WO | WO2011/143422 A1 | 11/2011 |
| WO | 2013/071088 A1 | 5/2013 |

OTHER PUBLICATIONS

Xianming Deng et al, 2012, "Leucine-rich repeat kinase 2 inhibitors: a patent review (2006-2011)" Expert Opinion on Therapeutic Patents, informa Healthcare GBR, vol. 22, No. 12, pp. 1415-1426, XP002722858.
International Search Report issued Apr. 7, 2014 in International Application No. PCT/EP2013/078105 filed Dec. 30, 2013.

*Primary Examiner* — Rebecca Anderson
(74) *Attorney, Agent, or Firm* — Mary Catherine Di Nunzio; Jeffrey I. Auerbach

(57) ABSTRACT

The present invention is directed to aminopyridine derived compounds of formula (A). The compounds are considered useful for the treatment of diseases associated with LRRK2 such a Lewy body dementia, Parkinson's disease or cancer.

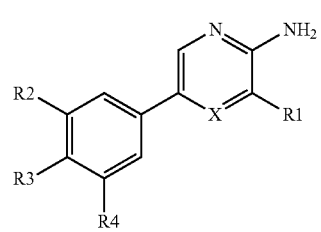

[A]

19 Claims, No Drawings

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Fluorescein-Labelled Peptide Substrate
      (Flouorescein-LRRKtide)

<400> SEQUENCE: 1

Gly Ala Gly Arg Leu Gly Arg Asp Lys Tyr Lys Thr Leu Arg Gln Ile
1               5                   10                  15

Arg Gln
```

AMINOPYRIDINE DERIVED COMPOUNDS AS LRRK2 INHIBITORS

CROSS-REFERENCE TO RELATED APPLICATIONS

The present application us a §371 U.S. National Stage Application or PCT International Application No. PCT/EP2013/078105, filed Dec. 30, 2013, which claims benefit of priority under 35 U.S.C. §119(e) of U.S. Provisional Application No. 61/743,142 filed Jan. 2, 2013, which claims benefit to U.S. Provisional Application No. 61/777,120, filed Mar. 12, 2013; which claims the benefit of priority under 35 U.S.C. §119(a)-(d) of Danish Application No. PA201300136, filed Mar. 11, 2013 and Danish Application No. PA201300004, filed Jan. 2, 2013.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entireties.

FIELD OF THE INVENTION

The present invention relates to aminopyridine derivatives which are LRRK2 inhibitors and thus useful in therapy and to pharmaceutical composition comprising said compounds.

BACKGROUND OF THE INVENTION

Parkinson's disease is a neurodegenerative disease. It is the second most common neurodegenerative disease after Alzheimer's disease and affects more than 1% of the population above the age of 65. Parkinson's disease is clinically characterised by resting tremor, bradykinesia and muscular rigidity. Pathologically, the disease is characterised by loss of dopaminergic neurons with the consequent decrease in dopamine levels in the brain and by aggregation of the protein α-synuclein in the dopaminergic neurons. These aggregations called Lewy-bodies are composed of insoluble α-synuclein phosphorylated at serine-129 and ubiquitin. Current Parkinson's disease therapeutic intervention strategies aim at increasing the dopamine levels in areas innervated by dopaminergic neurons in the brain. Levadopa is a precursor of dopamine, and it is therapeutically used to increase dopamine levels. Carbidopa is an inhibitor of the enzyme aromatic-L-amino-acid decarboxylase also known as DOPA decarboxylase, and it is often co-administered with levadopa to increase the fraction of levadopa which reaches the clinically relevant regions in the brain. Monoamine oxidase B inhibitors are administered to increase the levels of dopamine by blocking the metabolism of dopamine. As an alternative, dopamine agonists are administered to stimulate dopaminergic neurons, an effect similar to that obtained by increasing the dopamine levels. Although these therapies provide significant symptomatic benefit to the patient, they are also associated with adverse side effects and often become ineffective after prolonged treatment. Importantly, neither of the existing therapies addresses the underlying and disease causing problem, i.e. the progressive loss or inactivation of dopaminergic neurons.

Leucine-Rich Repeat Kinase 2 (LRRK2) is a 2527 amino acid protein involved in catalysing phosphorylation and GTP-GTD hydrolysis. The NCBI reference sequence for human LRKK2 mRNA is NM_198578.2. Evidence is mounting showing a relationship between LRRK2 and the pathogenesis of Parkinson's disease. It has been shown that LRRK2 phosphorylates α-synuclein at serine-129, and as discussed above this phosphorylated form constitutes a significant part of the Lewy-bodies [*BiochemBiophys Res Comm.,* 387, 149-152, 2009]. Additionally, single nucleotide polymorphisms in functional domains of LRRK2 have been shown to cause familiar and sporadic Parkinson's disease. So far at least 6 pathogenic variants have been identified, i.e. Gly2019Ser, Ile2020Thr, Arg1441Cys, Arg1441Gly, Arg1441His and Tyr1699Cys [*Parkinsonism Rel. Dis.,* 15, 466-467, 2009; *Movement Dis.,* 25, 2340-2345, 2010; *Neuron,* 44, 601-607, 2004; and *Lancet,* 365, 412-415, 2005]. Importantly, the clinical features of Parkinson's disease associated with LRRK2 mutations cannot be distinguished from those featuring in idiopathic Parkinson's disease. This strongly suggests a common pathogenic mechanism and that LRKK2 activity is a rate-limiting factor in Parkinson's disease progression [*FEBS Journal,* 276, 6436-6444, 2009].

The most common pathogenic form of LRRK2-associated Parkinson's disease is found in carriers of the amino acid substitution Gly2019Ser in the kinase domain of the LRRK2 protein. Gly2019Ser Parkinson's disease is inherited in an autosomal dominant fashion suggesting a gain-of-function mutation of the LRRK2 protein. In support of this notion, biochemical studies have shown that both the glycine to serine substitution at amino acid position 2019 as well as isoleucine to threonine substitution at amino acid position 2020 in the kinase domain lead to an increased kinase activity of LRRK2 [*Proc. Nat. Acad. Sci USA,* 102, 16842-16847, 2005]. This suggests a causal involvement of overactive LRRK2 in the pathogenesis of familiar forms of Parkinson's disease. Thus, inhibitors of LRRK2, including e.g. the G2019S and I2020T mutations, could be used as disease modifying treatment in familiar Parkinson's disease.

In cellular and animal studies several phosphorylation sites in the LRRK2 protein have been identified. Most prominent, phosphorylation of LRRK2 at two conserved residues serine at amino acid position 910 and serine at amino acid position 935 in human LRRK2 located just amino terminal to the leucine-rich repeat domain mediates binding to 14-3-3 proteins. Phosphorylation at serine residues 910 and 935 were shown to be dependent on an active LRRK2 conformation and further, that LRRK2 kinase inhibitors can inhibit phosphorylation at these two sites [*Biochem J.,* 430, 405-13, 2010; *J Neurochem.,* 120:37-45, 2012].

LRRK2 kinase inhibitors have been shown to concentration-dependently inhibit LRRK2-Ser910 and LRRK2-Ser935 phosphorylation in cellular models expressing LRRK2 and LRRK2-G2019S as well as human LRRK2-expressing lymphoblastoid cells from PD patients homozygous for the LRRK2 G2019S mutation. In addition, LRRK2 kinase inhibition dose-dependently inhibits LRRK2-Ser910 and LRRK2-Ser935 phosphorylation in mouse brain after in vivo administration of compound. [*ACS Med. Chem. Lett.,* DOI: 10.1021/ml300123a, 2012.].

Common single nucleotide polymorphisms of LRRK2 have also been associated with Parkinson's disease [*Nat Genet.* 2009 December; 41(12):1308-12*] [Mov Disorder.* Oct. 31, 2012; doi: 10.1002/mds.25226]. A recent genome wide association meta-analysis study where correction for G2019S carrier status was performed indicated that common LRRK2 variants with minor allele frequency (MAF) above 1% also are associated with an increased risk of Parkinson's disease [*Lancet.* 377, 641-649, 2011]. Further, investigations of common exonic polymorphic variants have highlighted several LRRK2 Parkinson's disease risk variants: in Caucasians the M1646T mutation, and in the Asian population the A419V mutation and also the previously found G2385R mutation [*Lancet Neurol.* 10, 898-908, 2011]. This indicates that LRRK2 inhibitors also could be useful as disease-modifying treatment in Parkinson's disease patients carrying common genomic LRRK2 variants such as M1646T, G2385R and A419V.

Indeed, as discussed above, as the clinical features of LRRK2 associated and idiopathic Parkinson's disease are very similar this also suggests that LRRK2 inhibitors could be useful for the treatment of sporadic PD.

As established above, LRRK2 inhibitors may by used in the treatment of Parkinson's disease and particular mention is made of Parkinson's disease associated with mutations in LRRK2, such as Gly2019Ser. Moreover, LRRK2 inhibitors are also expected to be useful in the treatment of other diseases which are associated with LRRK2. LRRK2 has been identified as a core component in Lewy bodies and is thus expected to be useful in the treatment of Lewy body dementia [*Neuropathol. Appl. Neurobiol.*, 34, 272-283, 2008]. Expression of LRRK2 mRNA is highly enriched in brain, lungs, kidney, spleen and blood suggesting that functional impact of increased LRRK2 activity is likely to be most relevant in pathogenic and pathologic conditions associated with those regions. Support for that notion can be found in studies showing an increased risk of non-skin cancer in LRRK2 Gly2019Ser mutation carriers and especially for renal and lung cancer [*Mov. Disorder*, 25, 2536-2541, 2010]. Overexpression of LRRK2 by chromosomal amplification has also been identified in papillary renal and thyroid carcinomas. Also, genetic association of LRRK2 has been reported to diseases in where aberrant responses of the immune system are involved. This is the case for inflammatory bowel diseases such as Crohn's disease and ulcerative colitis as well as for leprosy [*Nat Genet.* 42, 1118-1125, 2010; *Inflamm. Bowel. Dis.* 16, 557-558, 2010; *N Engl. J Med.* 361, 2609-2618, 2009; *Inflamm. Bowel. Dis.* doi: 10.1002/ibd.21651, 2011].

SUMMARY OF THE INVENTION

The present inventors have surprisingly found certain aminopyridine derivatives which are LRRK2 inhibitors. Accordingly, in one embodiment the invention provides compounds of formula A, below

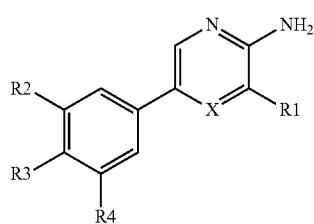

[A]

wherein
R1 represents triazolyl or oxadizolyl, said triazolyl or oxadizolyl may optionally be substituted with 1 R5 group,
X represents N or CH when R1 is triazolyl or when R1 is oxadiazole X represents CH,
R5 represents $C_1$-$C_6$ alkyl, $C_3$-$C_6$ cycloalkyl or a 5-6 membered heterocyclic ring with 1 or 2 heteroatom(s), said cycloalkyl or heterocyclic ring are optionally substituted with 1 or 2 $C_1$-$C_3$ alkyl or 1 or 2 $C_1$-$C_3$ alkoxy,
R2, R3 and R4 each independently represents hydrogen, halogen, $C_1$-$C_6$ alkyl, $C_1$-$C_6$ alkoxy, $O(CH_2)_nCF_3$, $(CH_2)_nR6$, $(C=O)R6$ or $(CH_2)_n(C=O)R6$, n=0, 1, 2 or 3, or
R2 and R3 or R3 and R4 may together with the atom they are attached to form a 9-10 membered bicyclic heterocyclic ring with 1 or 2 heteroatom(s), said bicyclic heterocyclic ring may optionally be substituted 1 or 2 $C_1$-$C_6$ alkyl or 1 or 2 $C_1$-$C_6$ alkoxy,
R6 represents a 5-6 membered heterocyclic ring with 1, 2 or 3 heteroatom(s), said heterocyclic ring may optionally be substituted with 1 or 2 $C_1$-$C_3$ alkyl or 1 or 2 $C_1$-$C_3$ alkoxy,
and pharmaceutically acceptable salts thereof.

In one embodiment, the invention provides a pharmaceutical composition comprising a compound of the above formula A and pharmaceutically acceptable salts thereof together with a pharmaceutically acceptable excipient.

In one embodiment, the invention provides compounds of the above formula A and pharmaceutically acceptable salts thereof for use in therapy.

In one embodiment, the invention provides compounds of the above formula A and pharmaceutically acceptable salts thereof for use in a method for the treatment of a disease associated with LRRK2.

In one embodiment, the invention relates to the use of a compound of the above formula A and pharmaceutically acceptable salts thereof in the manufacture of a medicament for use in the treatment of a disease associated with LRRK2.

In one embodiment, the invention relates to a method for the treatment of a disease associated with LRRK2, the method comprising the administration of a therapeutically effective amount of a compound of the above formula A and pharmaceutically acceptable salts thereof to a patient in need thereof.

DETAILED DESCRIPTION OF THE INVENTION

According to an embodiment of the invention the halogens in formula A hereinabove are independently selected from the group comprising fluoro, chloro, bromo or iodo and the heteroatoms may independently be selected from N, O or S.

Furthermore, the $C_1$-$C_6$ alkyl group may be selected from the group comprising methyl, ethyl, propyl, isopropyl, butyl, isobutyl, t-butyl, pentyl or isopentyl and the $C_1$-$C_3$ alkyl group may be selected from the group comprising methyl, ethyl, propyl, isopropyl.

The $C_1$-$C_6$ alkoxy group may be selected from the group comprising methoxy, ethoxy, propoxy, butoxy, isobutoxy, t-butoxy, pentoxy, isopropoxy and the $C_1$-$C_3$ alkoxy group may be selected from the group comprising methoxy, ethoxy, propoxy or isopropoxy.

In an embodiment R1 in formula A may be selected from the group comprising

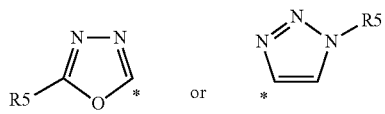

wherein * denotes the attachment point.

R5 in formula A may be selected from the group comprising $C_1$-$C_3$ alkyl, $C_3$-$C_6$ cycloalkyl or a heterocyclic ring selected from

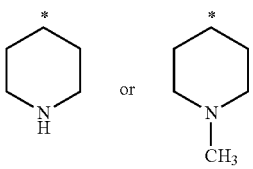

wherein * denotes the attachment point.
R2, R3 and/or R4 in formula A may be selected from the group comprising

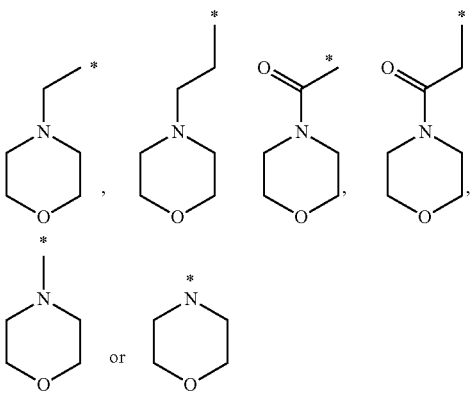

wherein * denotes the attachment point.
R2 and R3 or R3 and R4 may according to some embodiments form a bicyclic heterocyclic ring together with the atom they are attached selected from the group comprising

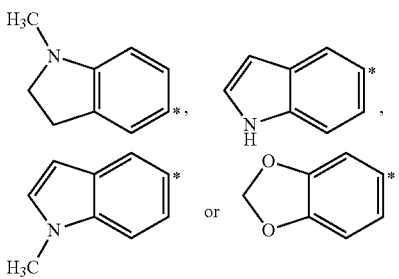

wherein * denotes the attachment point.
In a specific embodiment the compound are selected from the group comprising
5-(1H-Indol-5-yl)-3-(5-isopropyl-[1,3,4]oxadiazol-2-yl)-pyridin-2-ylamine,
3-(5-Cyclopropyl-[1,3,4]oxadiazol-2-yl)-5-(1H-indol-5-yl)-pyridin-2-ylamine,
3-(5-Cyclopropyl-[1,3,4]oxadiazol-2-yl)-5-(1-methyl-2,3-dihydro-1H-indol-5-yl)-pyridin-2-ylamine,
3-[5-(1-Methyl-piperidin-4-yl)-[1,3,4]oxadiazol-2-yl]-5-p-tolyl-pyridin-2-ylamine,
5-(1-Methyl-2,3-dihydro-1H-indol-5-yl)-3-(5-piperidin-4-yl-[1,3,4]oxadiazol-2-yl)-pyridin-2-ylamine,
3-(5-Cyclopropyl-[1,3,4]oxadiazol-2-yl)-5-(4-morpholin-4-ylmethyl-phenyl)-pyridin-2-ylamine,
5-(3-Methoxy-phenyl)-3-(5-piperidin-4-yl-[1,3,4]oxadiazol-2-yl)-pyridin-2-ylamine,
5-(3-Methoxy-phenyl)-3-[5-(1-methyl-piperidin-4-yl)-[1,3,4]oxadiazol-2-yl]-pyridin-2-ylamine,
3-(1-Isopropyl-1H-[1,2,3]triazol-4-yl)-5-(1-methyl-1H-indol-5-yl)-pyridin-2-ylamine,
3-(1-Isopropyl-1H-[1,2,3]triazol-4-yl)-5-(1-methyl-2,3-dihydro-1H-indol-5-yl)-pyridin-2-ylamine,
3-(1-Isopropyl-1H-[1,2,3]triazol-4-yl)-5-(1-methyl-2,3-dihydro-1H-indol-5-yl)-pyrazin-2-ylamine,
3-(1-Isopropyl-1H-[1,2,3]triazol-4-yl)-5-(4-morpholin-4-yl-methyl-phenyl)-pyridin-2-ylamine,
3-(1-Isopropyl-1H-[1,2,3]triazol-4-yl)-5-(4-morpholin-4-yl-phenyl)-pyridin-2-ylamine,
3-(1-Isopropyl-1H-[1,2,3]triazol-4-yl)-5-[4-(2-morpholin-4-yl-ethyl)-phenyl]-pyridin-2-ylamine,
5-(3-fluoro-4-(morpholinomethyl)phenyl)-3-(1-isopropyl-1H-1,2,3-triazol-4-yl)pyridin-2-amine,
(4-(6-amino-5-(1-isopropyl-1H-1,2,3-triazol-4-yl)pyridin-3-yl)-2-fluorophenyl)(morpholino)methanone,
[4-[6-amino-5-(1-isopropyltriazol-4-yl)-3-pyridyl]-2-methoxy-phenyl]-morpholino-methanone,
3-(1-isopropyltriazol-4-yl)-5-[3-methoxy-4-(morpholinomethyl)phenyl]pyridin-2-amine,
5-[4-fluoro-3-(morpholinomethyl)phenyl]-3-(1-isopropyl-triazol-4-yl)pyridin-2-amine,
[4-[6-amino-5-(1-isopropyltriazol-4-yl)-3-pyridyl]-2-methyl-phenyl]-morpholino-methanone,
3-(1-Isopropyltriazol-4-yl)-5-[3-methyl-4-(morpholinomethyl)phenyl]pyridin-2-amine,
[4-[6-amino-5-(1-isopropyltriazol-4-yl)-3-pyridyl]-2-chloro-phenyl]-morpholino-methanone,
5-[3-Chloro-4-(morpholinomethyl)phenyl]-3-(1-isopropyl-triazol-4-yl)pyridin-2-amine,
3-(1-Isopropyltriazol-4-yl)-5-[3-(morpholinomethyl)phenyl]pyridin-2-amine,
[3-[6-Amino-5-(1-isopropyltriazol-4-yl)-3-pyridyl]phenyl]-morpholino-methanone,
[3-[6-Amino-5-(1-isopropyltriazol-4-yl)-3-pyridyl]-5-chloro-phenyl]-morpholino-methanone,
5-[3-Chloro-5-(morpholinomethyl)phenyl]-3-(1-isopropyl-triazol-4-yl)pyridin-2-amine,
[4-[6-Amino-5-(1-isopropyltriazol-4-yl)-3-pyridyl]phenyl]-morpholino-methanone,
3-(5-cyclopropyl-1,3,4-oxadiazol-2-yl)-5-[3-(morpholinomethyl)phenyl]pyridin-2-amine,
2-[4-[6-amino-5-(1-isopropyltriazol-4-yl)-3-pyridyl]phenyl]-1-morpholino-ethanone,
or a pharmaceutical acceptable salt thereof.

The above mentioned compounds may be in a composition as the sole active ingredient or in combination with other active ingredients. Additionally one or more pharmaceutically acceptable carriers or diluents may be in the composition.

The compounds preferably have an IC50 value below 1000 nM.

The compounds of the present invention may have one or more asymmetric centres and it is intended that any optical isomers (i.e. enantiomers or diastereomers) as separated, pure or partially purified optical isomers and any mixtures thereof including racemic mixtures, i.e. a mixture of stereoisomers, are included within the scope of the invention.

In this context is understood that when specifying the enantiomeric form, the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In the present context, "pharmaceutically acceptable salts" include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

The term "aromatic" refers to a cyclic or polycyclic moiety having a conjugated unsaturated $(4n+2)\pi$ electron system (where n is a positive integer), sometimes referred to as a delocalized $\pi$ electron system. The term "heteroaromatic" intents to indicate an aromatic ring structure with one or more heteroatoms. Examples may include pyridinyl and pyrimidinyl.

In the present context, "alkyl" is intended to indicate a cyclic, straight or branched saturated hydrocarbon. In particular, $C_{1-6}$-alkyl is intended to indicate such hydrocarbon having 1, 2, 3, 4, 5 or 6 carbon atoms and likewise $C_{1-3}$-alkyl is intended to indicate a hydrocarbon having 1, 2 or 3 carbon atoms. Typical alkyl groups include, but are not limited to, methyl, ethyl, propyl, isopropyl, butyl, isobutyl, t-butyl, pentyl, isopentyl, hexyl and the like.

The term "alkoxy" as used herein refers to a group of formula —O-alkyl, wherein alkyl is defined as above. In particular, $C_1$-$C_6$-alkoxy is intended to indicate such hydrocarbon having 1, 2, 3, 4, 5 or 6 carbon atoms and likewise $C_1$-$C_3$-alkoxy indicate is intended to indicate a hydrocarbon having 1, 2 or 3 carbon atoms. Examples of alkoxy groups include, but are not limited to, methoxy, ethoxy, propoxy, butoxy, isobutoxy, t-butoxy, pentoxy, isopropoxy and the like.

In the present context, "halogen" is intended to indicate members of the $7^{th}$ main group of the periodic table of the elements, such as fluoro, chloro, bromo and iodo.

"Heteroatom" is intended to mean sulfur, oxygen or nitrogen.

The term "cyclic" as used herein refers to any cyclic structure, including alicyclic, heterocyclic, aromatic, heteroaromatic and polycyclic fused or non-fused ring systems. The term "membered" is meant to denote the number of skeletal atoms that constitute the ring. Thus, for example, pyridinyl, pyranyl, and pyrimidinyl are six-membered rings and pyrrolyl, tetrahydrofuranyl, and thiophenyl are five-membered rings.

Alkyl groups as described herein-above may according to some embodiments of the present invention also be cyclic. Examples of such types of alkyl groups include, but are not limited to cyclopropyl, cyclobutyl, cyclopentyl, cyclohexyl, cyclohexenyl, cycloheptenyl, and cyclooctanyl. The term "cycloalkyl" as used herein refers to a saturated monocyclic hydrocarbon radical. In particular $C_3$-$C_6$ cycloalkyl refers to a saturated monocyclic hydrocarbon radical having 3, 4, 5 or 6 carbon atoms.

The terms "heterocycle", "heterocyclic" and "heterocyclyl" as used herein, alone or in combination, refers to saturated or unsaturated nonaromatic rings containing from five to about 10 ring atoms where one or more of the ring atoms are heteroatoms.

In some embodiments of the invention a heterocylic ring is intended to mean a 5 or 6 membered cyclic ring structure with 1, 2 or 3 heteroatom(s).

The term "heterocyclic" may also include fused rings. A fused heterocyclic ring may contain from two to four fused rings where the attaching ring is a heterocyclic, and the other individual rings within the fused heterocyclic ring may be alicyclic, heterocyclic, aromatic, heteroaromatic or any combination thereof. Example of heterocyclics include, without limitation, morpholinyl, piperidinyl, tetrahydrofuranyl, benzodiazepinyl, tetrahydroindazolyl, dihydroquinolinyl, and the like.

In some embodiments the fused heterocyclic ring constitutes 2 fused rings which each may be saturated or unsaturated to form a "bicyclic heterocyclic ring" constituting a bicyclic ring structure of a total of 9-10 members. This bicyclic heterocyclic ring may have 1 or 2 heteroatoms in one or both of the rings.

Examples of "unsaturated heterocyclic groups" includes for example a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group and a pyrazinyl group; and "saturated heterocyclic group" such as a tetrahydropyranyl group, a tetrahydrothienyl group, a morpholinyl group, a thiomorpholinyl group, a pyrrolidinyl group, a pyrrolinyl group, an imidazolidinyl group, a pyrazolidinyl group, a piperidinyl group, a piperazinyl group, an oxazolidinyl group, an isoxazolidinyl group, a thiazolidinyl group, a pyrazolidinyl group, a dioxolanyl group and a dioxanyl group.

The terms "substituents" or "substituted" as used herein, alone or in combination, refer to groups which may be used to replace hydrogen. The substituted molecule may itself be further substituted in some embodiments of the invention.

In the present context, the term "therapeutically effective amount" of a compound is intended to indicate an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, e.g. by constructing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease from which the patient is suffering, such as administration of the active compound to alleviate the symptoms or complications, to delay the progression of the disease, to alleviate or relief the symptoms and complications, and/or to cure or eliminate the disease. The patient to be treated is preferably a mammal, in particular a human being. In the present context, "disease" can be used synonymously with disorder, condition, malfunction, dysfunction and the like.

As established above, LRRK2 inhibitors may by used in the treatment of Parkinson's disease and particular mention is made of Parkinson's disease associated with mutations in LRRK2, such as Gly2019Ser. Moreover, LRRK2 inhibitors are also expected to be useful in the treatment of other diseases which are associated with LRRK2. LRRK2 has been identified as a core component in Lewy bodies and is thus expected to be useful in the treatment of Lewy body dementia [*Neuropathol. Appl. Neurobiol.*, 34, 272-283, 2008]. Expression of LRRK2 mRNA is highly enriched in brain, lungs, kidney, spleen and blood suggesting that functional impact of increased LRRK2 activity is likely to be most relevant in pathogenic and pathologic conditions associated with those regions. Support for that notion can be found in studies showing an increased risk of non-skin cancer in LRRK2 Gly2019Ser mutation carriers and especially for renal and lung cancer [*Mov. Disorder*, 25, 2536-2541, 2010]. Over-expression of LRRK2 by chromosomal amplification has also been identified in papillary renal and thyroid carcinomas. Also, genetic association of LRRK2 has been reported for diseases where aberrant responses of the immune system are involved. This is the case for inflammatory bowel diseases such as Crohn's disease and ulcerative colitis as well as for leprosy [*Nat Genet.* 42, 1118-1125, 2010; *Inflamm. Bowel. Dis.* 16, 557-558, 2010; *N Engl. J Med.* 361, 2609-2618, 2009; *Inflamm. Bowel. Dis.* doi: 10.1002/ibd.21651, 2011].

Thus, the compounds, as outlined in formula A hereinabove, or composition comprising said compounds may be used in treatment of a disease or disorder characterised by over-expression of LRRK2 or a mutated form of LRRK2 such as G2019S, I2020T, M1646T, G2385R or A419V.

These disease or disorder may be a CNS disease selected from Lewy body dementia or Parkinson's disease, such as idiopathic Parkinson's disease or sporadic Parkinson's disease or in a Parkinson disease patient carrying anyone of the above mentioned LRRK2 mutations, in particular the G2019S mutation.

In a further embodiment, the compounds, as outlined in formula A hereinabove, or composition comprising said compounds may be used in the treatment of cancer or an immune related disorder characterised by over-expression of LRRK2 or a mutated form of LRRK2 such as G2019S, I2020T, M1646T, G2385R or A419V.

The cancer diseases may reside in the brain, lungs, kidney, spleen or blood organs such as renal cancer, lung cancer, skin cancer, and papillary renal and thyroid carcinomas.

The immune related disorder may in one embodiment be Chron's disease, ulcerative colitis or leprosy.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21 Edition, Mack Publishing Co, 2005. In the present context, "excipient", "carrier", "diluent", "adjuvant" and the like are used synonymously and are intended to mean the same.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Synthetic Routes

The compounds of the present invention of the general formula A herein above, wherein R1 to R6 are as defined above can be prepared by the methods outlined in the following reaction schemes and examples. In the described methods it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

Preparation of the Compounds of the Invention

The products of the invention can be prepared by the following general methods:

a) Reacting a compound of formula II or salt thereof with a boronic acid of formula III or a corresponding boronic acid ester in a suitable solvent such as a mixture of dioxane and water in the presence of a suitable catalyst such as tetrakis(triphenylphosphine)palladium and a suitable base such as or dicesium carbonate or potassium carbonate at a suitable temperature from 60° C.-150° C. The heating may be performed in a microwave system.

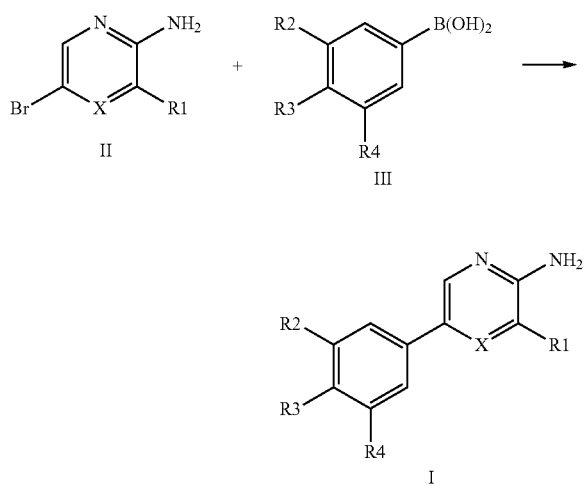

b) Where R2 and R3 together with the atom they are attached to form a compound as shown in formula V, the compounds of the invention can be prepared by reacting a compound of formula IV with TFA and triethylsilane at a suitable temperature such as 0° C.

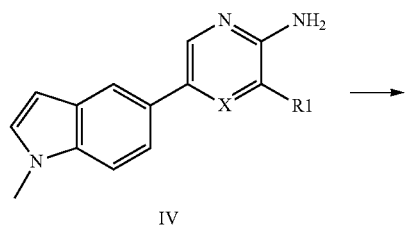

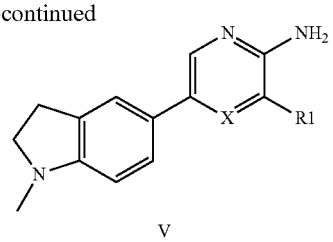

V c) Where the R1 group is as shown in formula VI the compounds of the invention can be prepare by removing a protecting group (PG) from a compound of formula VI. This utilises standard chemical transformations known to a person skilled in the art. This includes treating a compound of formula VI with where PG is COO$^t$Bu with a suitable acid such as hydrogen chloride in a suitable solvent such as ether and/or chloroform at a suitable temperature such as 0° C. to room temperature.

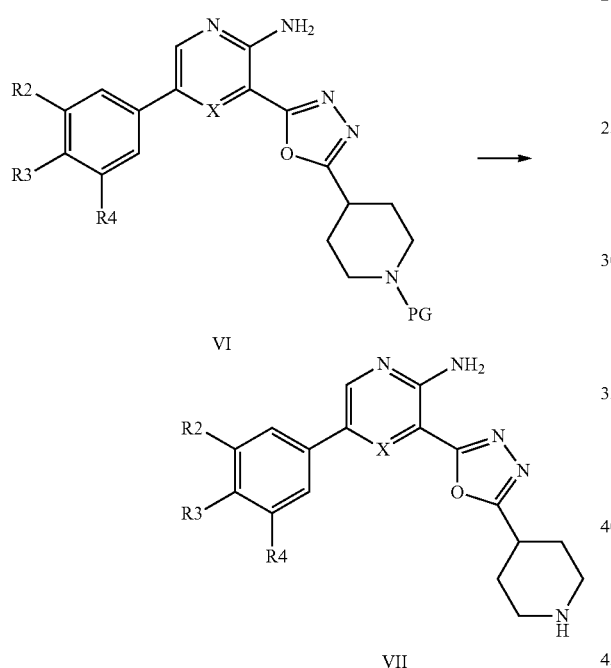

VI

VII d) Where the R1 group is as shown in formula IX the compounds of the invention can be prepared by alkylation of a compound of formula VIII using a suitable base such as NaH and a suitable alkylating reagent such as MeI in a suitable solvent such as THF at a suitable temperature such as 0° C.

VII

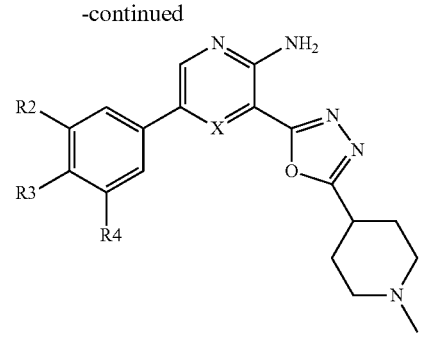

IX e) Where either the R2 or R3 group is (CO)R6 as shown in formula XV, the compounds of the invention can be prepared by reduction of the carbonyl. This can be done using a suitable reducing agent such as BH$_3$.DMS in a solvent such as THF at temperatures between 0° C. and 70° C.

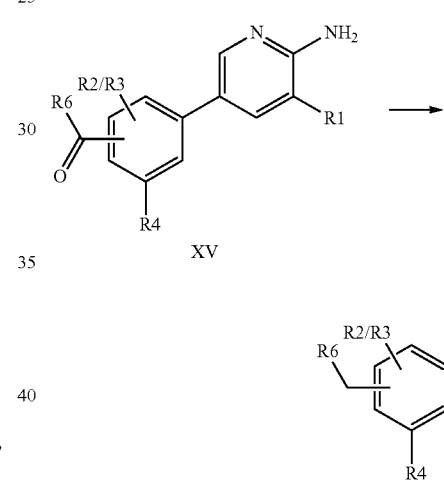

XV

XVI f) Compounds of the invention where R2 or R3 is (CO)R6 can be prepared by reacting a compound of formula XVII with R6H in the presence of an activating agent such as HATU or EDC together with HOBT in a suitable solvent (e.g. DMF) at a suitable temperature (such as room temperature (r.t)). The reaction may take place in the presence of a base (e.g. triethylamine).

g)

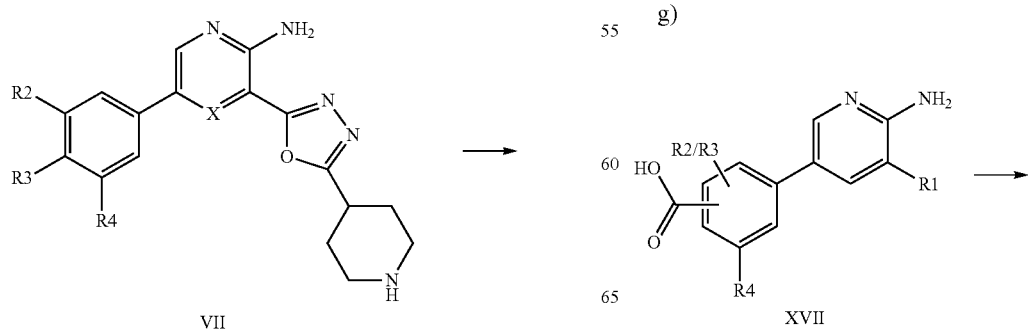

XVII

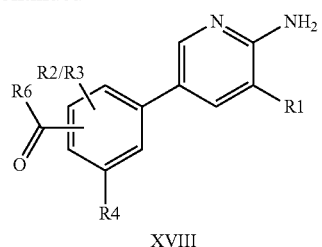

XVIII

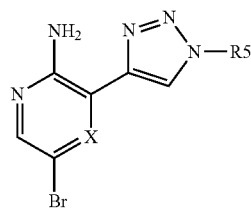

IIB

Compounds of formula II or salts thereof, where X=CH and R1 is an [1,3,4]oxadiazole, can be prepared by reacting a compound of formula XI with a hydrazide of formula XII in POCl$_3$ at suitable temperatures such as between room temperature and 100° C.

Alternatively the reaction can be performed by reacting a compound of formula XI with a hydrazide of formula XII in a suitable solvent such as DMF in the presence of an activating agent such as HATU in the presence of a base such as DIPEA at a suitable temperature such as room temperature. The product of this reaction can ring close by treatment with PPh$_3$, DBU and CCl$_4$ in a suitable solvent such as acetonitrile at a suitable temperature such as room temperature.

Synthesis of compounds of formula IV, VI and XV can be carried out as described above for a).

Compounds of formula III where R2 or R3 are (CO)R6 can be prepared by reacting can be prepared by reacting a compound of formula XIX with R6H in the presence of an activating agent such as HATU or EDC together with HOBT in a suitable solvent (e.g. DMF) at a suitable temperature (such as room temperature (r.t)). The reaction may take place in the presence of a base (e.g. triethylamine).

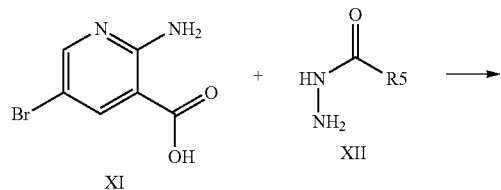

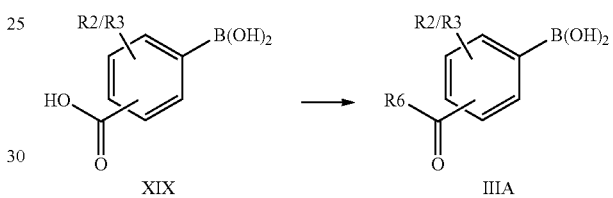

Compounds of formula XXI can be prepared by reacting a compound of formula II or salt hereof by methods described above in a). Compounds of formula XXI can be hydrolysed using a suitable base such as LiOH in a solvent such as a mixture of dioxane and water at a temperature between room temperature and 100° C. to give compounds of formula XVII.

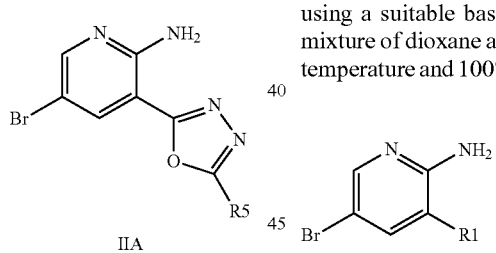

IIA

Compounds of formula II or salts thereof where C=CH and R1 is an [1,2,3]triazole can be prepared by reaction of a compound of formula XIII with sodium azide in a suitable solvent such as a mixture of butanol and water at a suitable temperature such as 80° C. followed by addition of a compound of formula XV and CuI.

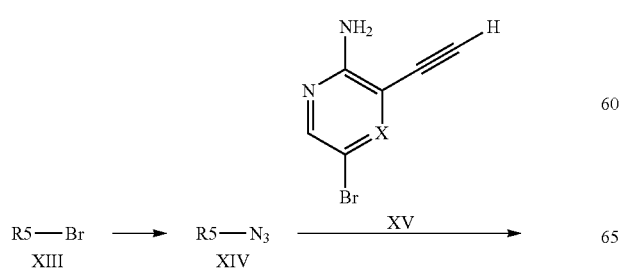

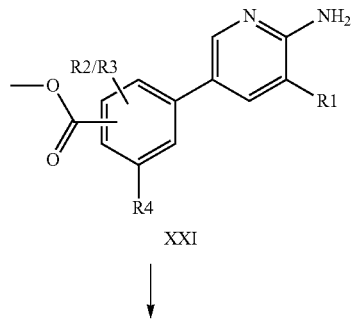

XXI

-continued

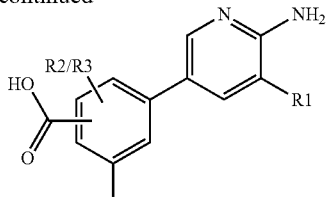

XVII

EXPERIMENTAL

General Methods $^1$H NMR spectra were recorded at 400 MHz on a Varian 400MR instrument at T=298.15 K or at 400 MHz on a Varian vnmrs instrument. Deuterated solvents (CDCl$_3$, DMSO-d$_6$, CD$_3$OD) were used for preparation. Tetramethylsilane was used as internal reference standard. Chemical shift values are expressed in ppm-values relative to tetramethylsilane unless noted otherwise.

Method A
Waters Acquity UPLC-MS
 (Bin. Solv. manager, col. manager, PDA, ELSD, Sample manager+organizer, SQD)
 Duration 1.15 min
 Column type: Acquity UPLC BEH C18 1.7 μm; 2.1×50 mm
 Column temperature: 60° C.
 PDA: 254 nm
 Desolvation temp.: 350° C.
 Ion source: ESCI+/−
 Source temp.: 150° C.
 Make-up flow: 0.5 ml/min. EtOH
 Flow: 1.2 ml/min.
 Solvents:
A: Water containing 0.1% Formic acid
B: Acetonitrile containing 5% Water and 0.1% Formic acid

|  | Time, min. | % B | Curve |
|---|---|---|---|
| Gradient: | 0.00 | 10.0 | 6 |
|  | 1.00 | 99.9 | 6 |
|  | 1.01 | 10.0 | 6 |
|  | 1.15 | 10.0 | 6 |

Method B
Waters Acquity UPLC-MS
 Bin. Solv. manager, col. manager, PDA, ELSD, Sample manager, TQD)
 Duration 1.15 min
 Column type: Acquity UPLC BEH C18 1.7 μm; 2.1×50 mm
 Column temperature: 60° C.
 PDA: 254 nm
 Probe temp.: 450° C.
 Source temp.: 150° C.
 Ion source: APPI pos.
 Dopant flow: 0.04 ml/min. Toluene
 Flow: 1.2 ml/min.
 Solvents:
A: Water containing 0.05% TFA
B: Acetonitrile containing 5% Water and 0.035% TFA

|  | Time, min. | % B | Curve |
|---|---|---|---|
| Gradient: | 0.00 | 10.0 | 6 |
|  | 1.00 | 100 | 6 |
|  | 1.01 | 10.0 | 6 |
|  | 1.15 | 10.0 | 6 |

Abbreviations
RT: room temperature
BINAP: 2,2'-bis(diphenylphosphino)-1,1'-binaphthyl
DMF: Dimethylformamide
DCM: Dichloromethane
EtOAc: Ethylacetate
HATU: N,N,N',N'-tetramethyl-O-(7-azabenzotriazol-1-yl)uronium hexafluorophosphate
DIPEA: N,N-Diisopropylethylamine
DBU: 1,8-Diazabicycloundec-7-ene
THF: Tetrahydrofuran
TFA: Trifluoroacetic acid
ACN: Acetonitrile
TLC: thin layer chromatography 2-Amino-5-bromo-nicotinic acid

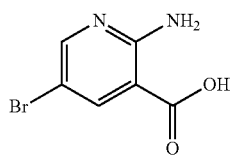 [SMILES: Nc1ncc(Br)cc1C(=O)O]

To a solution of pyridine-2-amino-3-carboxylic acid (2.05 g, 81.1 mmol) in AcOH (250 mL) was added bromine (11.0 mL, 199.2 mmol) at RT. The reaction mixture was stirred for 18 h at RT. On completion of the reaction, the solvent was evaporated completely under reduced pressure, filtered, washed with diethyl ether (3×75 mL) to afford the title compound as a yellow solid.
Yield: 50.0 g (92.6%)
$^1$HNMR (DMSO-d$_6$, 400 MHz, TMS) δ: 11.7 (3H, br, s), 8.33 (1H, s), 8.20 (1H, s).

5-Bromo-3-(5-cyclopropyl-[1,3,4]oxadiazol-2-yl)-pyridin-2-ylamine

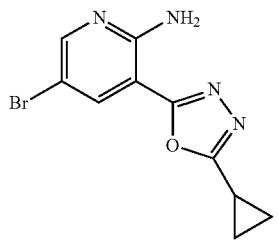 [SMILES: Nc1ncc(Br)cc1-c1nnc(C2CC2)o1]

A solution of 2-amino-5-bromo-nicotinic acid (300 mg, 1.38 mmol) and cyclopropanecarboxylic acid hydrazide (300 mg, 3.0 mmol) in POCl$_3$ (30.0 mL) was stirred for 18 h at 65° C. The reaction mixture was distilled under reduced pressure to obtain a residue, which was cooled to 0° C. by adding iced water and neutralizing with saturated NaHCO$_3$ solution (100 mL). The aqueous layer was extracted with ethyl acetate. The ethyl acetate layer was separated, dried over anhydrous Na$_2$SO$_4$ and evaporated to afford 370 mg of crude 5-bromo-3-(5-cyclopropyl-[1,3,4]oxadiazol-2-yl)-pyridin-2-ylamine. Crude compound was purified by column chromatography using silica gel (100-200 mesh). The column was eluted with 15% EtOAc in petroleum ether to afford the title compound as a pale yellow solid used without further purification.
Yield: 300 mg (Yield: 81%)

5-Bromo-3-(5-isopropyl-[1,3,4]oxadiazol-2-yl)-pyridin-2-ylamine

To a solution of 2-amino-5-bromo-nicotinic acid (1.0 g, 4.60 mmol) in POCl$_3$ (20 mL) was added isobutyric acid hydrazide (705 mg, 6.912 mmol) at RT. The reaction temperature was slowly heated to 100° C. and stirred for 18 h. The solvent was evaporated under reduced pressure, the residue was basified with saturated cold sodium bicarbonate solution (50 mL), extracted with ethyl acetate (3×50 mL), organic layer was washed with brine, dried over anhydrous sodium sulphate and concentrated under reduced pressure. Crude compound was purified by column chromatography using 100-200 mesh silica gel. The column was eluted with 40% EtOAc in petroleum ether to afford the title compound as a yellow solid.
Yield: 650 mg (50%)
$^1$HNMR (DMSO-d$_6$, 400 MHz, TMS) δ: 8.28-8.27 (1H, d), 8.18-8.17 (1H, d), 7.45 (2H, br, s), 3.32-3.24 (1H, m), 1.38-1.37 (6H, d).

3-(5-Cyclopropyl-[1,3,4]oxadiazol-2-yl)-5-(1-methyl-1H-indol-5-yl)-pyridin-2-ylamine

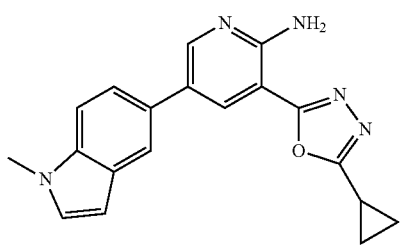 [SMILES: Cn1ccc2cc(-c3cnc(N)c(-c4nnc(C5CC5)o4)c3)ccc21]

To a solution of 5-bromo-3-(5-cyclopropyl-[1,3,4]oxadiazol-2-yl)-pyridin-2-ylamine (500 mg, 1.77 mmol) in dioxane (15.0 mL) and water (5.0 mL) were added K$_2$CO$_3$ (730 mg, 5.31 mmol) and N-methylindole-5-boronic acid (140 mg, 1.95 mmol) in a sealed tube. The reaction mixture was degassed with argon for 20 min, then Pd(PPh$_3$)$_4$ (100 mg, 0.088 mmol) was added and stirred for 18 h at 100° C. The reaction mixture was diluted with water (20 mL) and extracted with ethyl acetate (3×20 mL). The organic layer was washed with brine, dried over anhydrous sodium sulphate and concentrated under reduced pressure to get crude title compound. Crude product was purified by column chromatography using 100-200 mesh silica gel and compound was eluted with 40% ethyl acetate in petroleum ether to afford the title compound.
Yield: 350 mg (61%)
$^1$HNMR (DMSO-d$_6$, 400 MHz, TMS) δ: 8.54-8.53 (1H, d), 8.22-8.21 (1H, d), 7.82-7.81 (1H, d), 7.53-7.51 (1H, d), 7.46-7.44 (1H, d), 7.36-7.35 (1H, d), 7.25 (2H, broad s, NH$_2$), 6.48-6.47 (1H, d), 3.82 (3H, s), 2.36-2.33 (m, 1H), 1.20-1.18 (4H, d).

4-[N'-(2-Amino-5-bromo-pyridine-3-carbonyl)-hydrazinocarbonyl]-piperidine-1-carboxylic acid tert-butyl ester

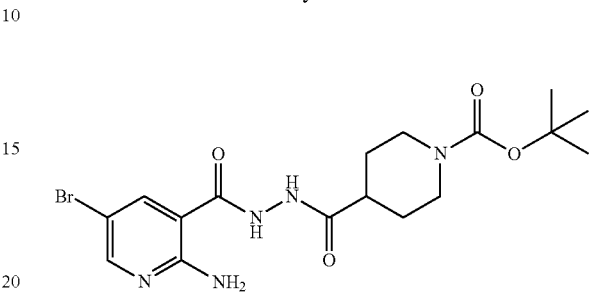

To a solution of 2-amino-5-bromo-nicotinic acid (1.2 g, 5.53 mmol) in DMF (30 mL) were added 4-hydrazinocarbonyl-piperidine-1-carboxylic acid tert-butyl ester (1.5 g, 6.173 mmol), HATU (2.35 g, 6.184 mmol) and DIPEA (4 mL, 23.56 mmol) at RT. The reaction mixture was stirred for 18 h at RT. The reaction mixture was poured into ice-water (30 mL), extracted with ethyl acetate (3×50 mL), organic layer was washed with brine dried over anhydrous sodium sulphate concentrated under reduced pressure. Crude compound was purified by column chromatography using 100-200 mesh silica gel. The column was eluted with 60% EtOAc in petroleum ether to afford the title compound as an off-white solid.
Yield: 1.3 g (53.19%)
$^1$HNMR (DMSO-d$_6$, 400 MHz, TMS) δ: 10.32 (1H, s), 9.92 (1H, s), 8.20 (1H, s), 8.12-8.11 (1H, d), 7.2 (2H, s), 3.96-3.94 (2H, m), 2.77-2.69 (2H, m), 2.50-2.41 (1H, m), 1.73-1.70 (2H, m), 1.49-1.44 (2H, m), 1.40 (9H, s).

4-[5-(2-Amino-5-bromo-pyridin-3-yl)-[1,3,4]oxadiazol-2-yl]-piperidine-1-carboxylic acid tert-butyl ester

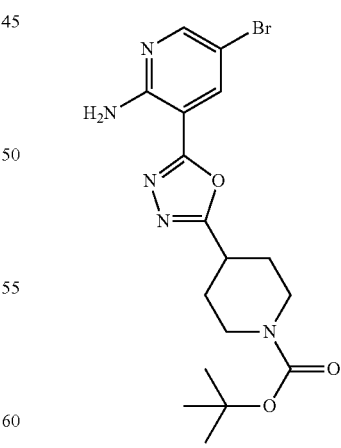

To a solution of 4-[N'-(2-amino-5-bromo-pyridine-3-carbonyl)-hydrazinocarbonyl]-piperidine-1-carboxylic acid tert-butyl ester (1.3 g, 2.939 mmol) in ACN (50 mL) were added DBU (1.68 g, 11.035 mmol), PPh$_3$ (1.95 g, 7.434 mmol) and CCl$_4$ (4 mL, 41.558 mmol) at RT. The reaction mixture was stirred for 18 h at RT. The reaction mixture was poured into ice-water (30 mL), extracted with ethyl acetate (3×50 mL), organic layer was washed with brine dried over anhydrous sodium sulphate concentrated under reduced pressure. Crude compound was purified by column chromatography using 100-200 mesh silica gel. The column was eluted with 40% EtOAc in petroleum ether to afford the title compound as a white solid.

Yield: 700 mg (56.4%)

$^1$HNMR (DMSO-$d_6$, 400 MHz, TMS) δ: 8.28-8.27 (1H, d), 8.21-8.20 (1H, d), 7.44 (2H, br, s), 7.2 (2H, s), 3.95-3.91 (2H, m), 3.31-3.23 (1H, m), 2.99 (2H, br, s), 2.08-2.04 (2H, m), 1.74-1.64 (2H, m), 1.41 (9H, s).

4-{5-[2-Amino-5-(1-methyl-H-indol-5-yl)-pyridin-3-yl]-[1,3,4]oxadiazol-2-yl}-piperidine-1-carboxylic acid tert-butyl ester

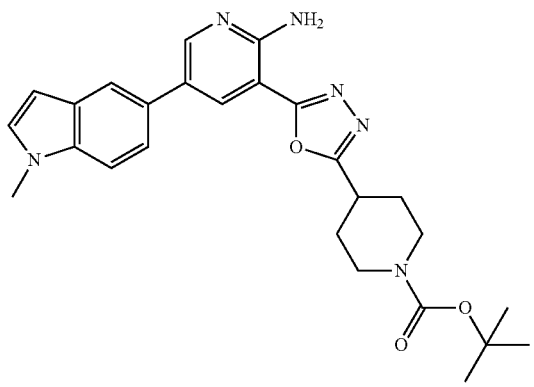 [SMILES: Cn1ccc2cc(-c3cnc(N)c(-c4nnc(C5CCN(C(=O)OC(C)(C)C)CC5)o4)c3)ccc21]

To a solution of 4-[5-(2-amino-5-bromo-pyridin-3-yl)-[1,3,4]oxadiazol-2-yl]-piperidine-1-carboxylic acid tert-butyl ester (1.1 g, 2.59 mmol) in dioxane (20 mL) and water (10 mL) were added $K_2CO_3$ (1.07 g, 7.77 mmol) and N-methylindole-5-boronic acid (0.50 g, 2.85 mmol) in a sealed tube. The reaction mixture was degassed with argon for 20 min, then Pd(PPh$_3$)$_4$ (0.15 g, 0.13 mmol) was added to the reaction mixture. The reaction mixture was stirred for 18 h at 100° C. The reaction was diluted with water (100 mL), extracted with ethyl acetate (2×150 mL) and organic layer was washed with brine, dried over anhydrous sodium sulphate and concentrated under reduced pressure to get crude compound. Crude compound was purified by column chromatography using 100-200 mesh silica gel compound eluted with 60% ethyl acetate in petroleum ether to afford 900 mg of the title compound which is further purified by washing with 20% chloroform in hexane to afford the title compound as a pale yellow solid.

Yield: 700 mg (56.9%)

$^1$HNMR (DMSO-$d_6$, 400 MHz, TMS) δ: 8.56-8.55 (1H, d), 8.28-8.27 (1H, d), 7.82 (1H, s), 7.53-7.51 (1H, d), 7.47-7.44 (1H, d), 7.36-7.35 (1H, d), 7.30-7.26 (2H, broad s), 6.48-6.47 (1H, d), 3.97-3.94 (2H, d), 3.82 (3H, s), 3.30-3.27 (1H, m), 3.05-2.92 (2H, m), 2.12-2.08 (2H, d), 1.76-1.66 (2H, m), 1.41 (9H, s).

4-[5-(2-Amino-5-p-tolyl-pyridin-3-yl)-[1,3,4]oxadiazol-2-yl]-piperidine-1-carboxylic acid tert-butyl ester

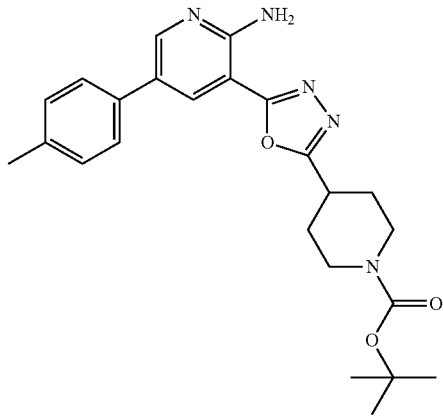 [SMILES: Cc1ccc(-c2cnc(N)c(-c3nnc(C4CCN(C(=O)OC(C)(C)C)CC4)o3)c2)cc1]

To a solution of 4-[5-(2-amino-5-bromo-pyridin-3-yl)-[1,3,4]oxadiazol-2-yl]-piperidine-1-carboxylic acid tert-butyl ester (500 mg, 1.179 mmol) in dioxane (20 mL) and water (10 mL) were added $K_2CO_3$ (488 mg, 3.537 mmol) and 4-tolyl boronic acid (179 mg, 1.297 mmol) in a sealed tube. The reaction mixture was degassed with $N_2$ for 20 min, then Pd(PPh$_3$)$_4$ (136 mg, 0.118 mmol) was added to the reaction mixture at RT, The reaction mixture temperature was raised to 100° C., stirred for 18 h at 100° C. The reaction mixture was diluted with water (30 mL) extracted with ethyl acetate (3×30 mL) and organic layer was washed with brine, dried the organic layer over anhydrous sodium sulphate and concentrated under reduced pressure to affords the crude product. Crude was purified by column chromatography using 100-200 mesh silica gel compound eluted with 35% ethyl acetate in petroleum ether to afford the title compound as a white solid.

Yield: 250 mg, (48.8%)

$^1$HNMR (DMSO-$d_6$, 400 MHz, TMS) δ: 8.54 (1H, s), 8.25 (1H, s), 7.59-7.57 (2H, m), 7.36 (2H, br, s), 7.28-7.26 (2H, m), 3.96-3.93 (2H, m), 3.32 (1H, m), 2.998 (2H, br, s), 2.34 (3H, s), 2.10-2.08 (2H, m), 1.75-1.67 (2H, m), 1.41 (9H, s).

3-(5-Piperidin-4-yl-[1,3,4]oxadiazol-2-yl)-5-p-tolyl-pyridin-2-ylamine

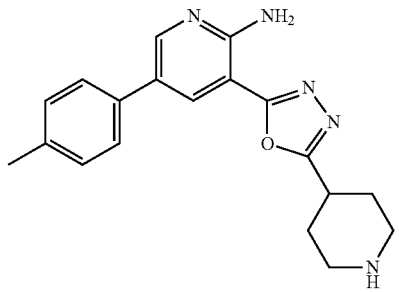 [SMILES: Cc1ccc(-c2cnc(N)c(-c3nnc(C4CCNCC4)o3)c2)cc1]

To a solution of 4-[5-(2-amino-5-p-tolyl-pyridin-3-yl)-[1,3,4]oxadiazol-2-yl]-piperidine-1-carboxylic acid tert-butyl ester (250 mg, 0.574 mmol) in DCM (20 mL) was added 2M HCl in diethyl ether (20 mL) at 0° C. The reaction mixture was allowed to warm to ambient temperature, and was stirred for 2 h. After completion of the reaction, reaction mixture was filtered and washed with diethyl ether (2×30 mL), which afforded the title compound as a yellow solid.

Yield: 200 mg (93.8%)

¹HNMR (DMSO-d₆, 400 MHz, TMS) δ: 8.80 (1H, s), 8.57-8.56 (2H, d), 8.28-8.27 (1H, s), 7.59-7.57 (2H, m), 7.49 (1H, br, s), 7.30-7.28 (2H, m), 3.51 (1H, m), 3.37-3.34 (2H, m), 3.17-3.08 (2H, m), 2.35 (3H, s), 2.32-2.28 (2H, m), 2.07-1.98 (2H, m).

4-{5-[2-Amino-5-(3-methoxy-phenyl)-pyridin-3-yl]-[1,3,4]oxadiazol-2-yl}-piperidine-1-carboxylic acid tert-butyl ester

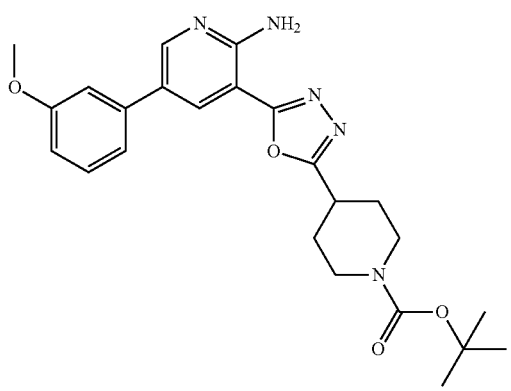 [SMILES: COc1cccc(-c2cnc(N)c(-c3nnc(C4CCN(C(=O)OC(C)(C)C)CC4)o3)c2)c1]

To a solution of 4-[5-(2-amino-5-bromo-pyridin-3-yl)-[1,3,4]oxadiazol-2-yl]-piperidine-1-carboxylic acid tert-butyl ester (1.0 g, 2.35 mmol) in dioxane (20 mL) and water (20 mL) were added K₂CO₃ (0.95 g, 7.05 mmol), 3-methoxyphenyl boronic acid (0.39 g, 2.59 mmol) in a sealed tube. The reaction mixture was degassed with argon for 20 min, then Pd(PPh₃)₄ (0.13 g, 0.11 mmol) was added to the reaction mixture. The reaction mixture was stirred for 18 h at 100° C. The reaction mixture was diluted with water (100 mL) extracted with ethyl acetate (2×150 mL) and organic layer was washed with brine, dried over anhydrous sodium sulphate and concentrated under reduced pressure to get crude product. The crude compound was purified by column chromatography using 100-200 mesh silica gel and compound was eluted with 40% ethyl acetate in petroleum ether to afford 500 mg, which was further purified by washing with diethyl ether and hexane to afford the title compound as a pale yellow solid.

Yield: 400 mg (37.7%)

¹HNMR (DMSO-d₆, 400 MHz, TMS) δ: 8.57-8.56 (1H, d), 8.28-8.27 (1H, d), 7.42-7.35 (3H, m), 7.25-7.21 (2H, m), 6.93-6.91 (1H, dd), 3.96-3.93 (2H, d), 3.83 (3H, s), 3.30-3.26 (1H, m), 3.03-2.95 (2H, m), 2.11-2.08 (2H, d), 1.76-1.65 (2H, m), 1.41 (9H, s).

5-Bromo-3-(1-isopropyl-H-[1,2,3]triazol-4-yl)-pyridin-2-ylamine

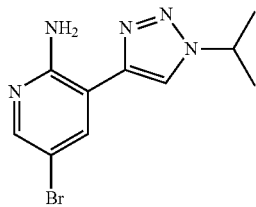 [SMILES: CC(C)n1cc(-c2cc(Br)cnc2N)nn1]

A mixture of isopropyl bromide (5.0 g, 40.65 mmol) and sodium azide (2.6 g, 40.65 mmol) in t-BuOH/water (1:2) (50 mL) was stirred for 2 h at 80° C. Then the reaction mixture was cooled to room temperature, to which was added 5-bromo-3-ethynyl-pyridin-2-ylamine (0.8 g, 4.065 mmol) and CuI (catalytic amount). The reaction mixture was stirred for 16 h at 80° C. The reaction mixture was cooled to RT, diluted with EtOAc (100 mL) and washed with water (50 mL). The organic layer was washed with brine solution (50 mL), dried over anhydrous Na₂SO₄ and solvent was evaporated under reduced pressure to afford crude compound. Crude compound was washed with diethyl ether to afford the title compound as ash colour solid.

Yield: 450 mg (40.9%)

¹H NMR (DMSO-d₆, 400 MHz, TMS) δ: 8.87 (1H, s), 8.09-8.08 (1H, d), 8.04 (1H, s), 7.15 (2H, br), 4.90-4.83 (1H, m), 1.55 (3H, s), 1.53 (3H, s).

5-Bromo-3-(1-isopropyl-1H-[1,2,3]triazol-4-yl)-pyrazin-2-ylamine

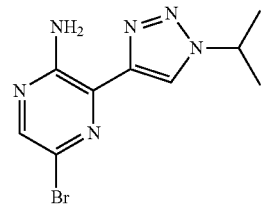 [SMILES: CC(C)n1cc(-c2nc(Br)cnc2N)nn1]

A mixture of isopropyl bromide (2.5 g, 20.3 mmol) and sodium azide (1.3 g, 20.3 mmol) in t-BuOH/water (1:2) (25 mL) was stirred for 2 h at 80° C. Then the reaction mixture was cooled to room temperature, was added 5-bromo-3-ethynyl-pyrazin-2-ylamine (0.40 g, 2.03 mmol) and CuI (catalytic amount) and stirred for 16 h at 80° C. The reaction mixture was cooled to RT, diluted with EtOAc (100 mL) and washed with water (50 mL). The organic layer was washed with brine solution (50 mL), dried over anhydrous Na₂SO₄ and solvent was evaporated under reduced pressure to afford crude product. The crude product was washed with diethyl ether to afford the title compound as a solid.

Yield: 370 mg (64.7%)

¹H NMR (DMSO-d₆, 400 MHz, TMS) δ: 8.82 (1H, s), 8.11 (1H, s), 7.55 (2H, s, br), 4.97-4.90 (1H, m), 1.57-1.55 (6H, d).

3-(1-Isopropyl-1H-[1,2,3]triazol-4-yl)-5-(1-methyl-H-indol-H-indol-5-yl)-pyrazin-2-ylamine

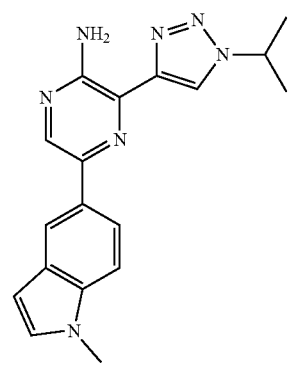 [SMILES: CC(C)n1cc(-c2nc(-c3ccc4c(ccn4C)c3)cnc2N)nn1]

To a solution of 5-bromo-3-(1-isopropyl-1H-[1,2,3]triazol-4-yl)-pyrazin-2-ylamine (750 mg, 2.65 mmol) and N-methylindole-5-boronic acid (556 mg, 3.18 mmol) in 1,4-dioxane (15.0 mL)/water (5.0 mL) was added $Cs_2CO_3$ (1.29 g, 3.97 mmol) at room temperature. The reaction mixture was purged with argon for 30 min. Then $Pd(PPh_3)_4$ (153 mg, 0.13 mmol) was added and allowed to stir at 100° C. for 16 h. The reaction mixture was cooled to RT, diluted with EtOAc (20 mL) and washed with water (20 mL). The organic layer was washed with brine solution (20 mL), dried over anhydrous $Na_2SO_4$ and solvent was evaporated under reduced pressure to afford crude product. The crude compound was purified by column using 100-200 mesh silica gel. The column was eluted with 70-80% EtOAc in Hexane to afford the title compound as a yellow solid.

Yield: 610 mg (69.1%)

$^1$H NMR (DMSO-$d_6$, 400 MHz, TMS) δ: 8.95 (1H, s), 8.60 (1H, s), 8.27 (1H, d), 7.92-7.90 (1H, dd), 7.50-7.48 (1H, d), 7.35 (1H, d), 7.30 (2H, br), 6.49-6.48 (1H, d), 5.02-4.95 (1H, m), 3.82 (3H, s), 1.62-1.60 (6H, d).

2-(4-Iodo-phenyl)-1-morpholin-4-yl-ethanone

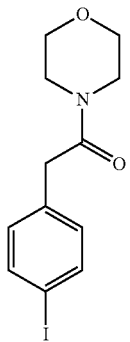

Triethylamine (5.30 mL, 38.0 mmol), HOBt (3.96 g, 28.5 mmol) and EDC.HCl (5.47 g, 28.5 mmol) were added to a solution of (4-iodo-phenyl)-acetic acid (5.0 g, 19.0 mmol) in DMF (100 mL) and stirred. After 5 min morpholine (2.0 mL, 22.9 mmol) was added at RT. The reaction mixture was stirred at RT for 16 h. The reaction mixture was poured into ice-cold water (50 mL) and obtained solid was filtered, dried to get 3.92 g (Yield: 62.1%) of the title compound as a white solid.

$^1$H NMR (DMSO-$d_6$, 400 MHz, TMS) δ: 7.66-7.64 (2H, d), 7.04-7.02 (2H, d), 3.68 (2H, s), 3.54-3.42 (8H, m).

4-[2-(4-Iodo-phenyl)-ethyl]-morpholine

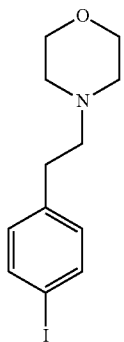

$BF_3.Et_2O$ (6.43 g, 45.3 mmol) was added to a solution of 2-(4-iodo-phenyl)-1-morpholin-4-yl-ethanone (3.0 g, 9.06 mmol) in THF (75 mL) at 0° C., stirred for 30 min, then $NaBH_4$ (1.72 g, 45.3 mmol) was added at 0° C. The reaction mixture was slowly warmed to RT. After 16 h the reaction mixture was cooled to 0° C., quenched with ice-cold water, extracted with EtOAc (2×100 mL). The organic layer was washed with brine solution (50 mL), dried over anhydrous $Na_2SO_4$ and solvent was evaporated under reduced pressure. The crude compound was purified by column chromatography using 100-200 mesh silica gel, eluted with 20-30% EtOAc in pet-ether to afford 1.56 g (Yield: 54.3%) of the title compound as a yellow solid.

$^1$H NMR (DMSO-$d_6$, 400 MHz, TMS) δ: 7.64-7.62 (2H, d), 7.07-7.05 (2H, d), 4.11-4.07 (2H, q), 3.58 (4H, br, s), 2.67 (2H, br, s), 2.46 (4H, br, s).

4-{2-[4-(4,4,5,5-Tetramethyl-[,3,2]dioxaborolan-2-yl)-phenyl]-ethyl}-morpholine

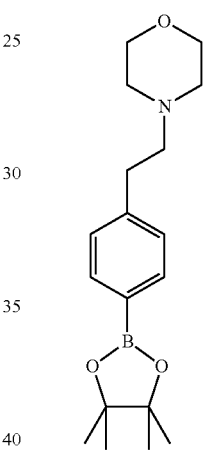

To a solution of 4-[2-(4-iodo-phenyl)-ethyl]-morpholine (250 mg, 0.78 mmol) and 4,4,5,5,4',4',5',5'-Octamethyl-[2,2']bi[[1,3,2]dioxaborolanyl](240 mg, 0.94 mmol) in DMSO (15.0 mL) was added KOAc (191 mg, 1.95 mmol) at RT. $N_2$ was purged through the reaction mixture for 10 min. Then $Pd(dppf)Cl_2.DCM$ (31.8 mg, 0.039 mmol) was added and through the reaction mixture $N_2$ was purged for 10 min and stirred at 100° C. for 16 h. Reaction mixture was cooled to RT, diluted with EtOAc (50 mL) and washed with water (50 mL). Organic layer was washed with brine solution (50 mL), dried over anhydrous $Na_2SO_4$ and solvent was evaporated under reduced pressure. Crude compound was purified by column chromatography using 100-200 mesh silica gel and eluted with 40-50% EtOAc in Pet-ether to afford 110 mg (Yield: 44.0%) of the title compound as brown semi-solid.

LCMS Conditions:

Column: SYMMETRY C18 (4.6×75 mm); 3.5u

M-Phase A: 5 mM Ammonium Acetate in $H_2O$

M-Phase B: ACN

T/% B: 0/05, 2.5/98, 8.0/98, 8.1/5

Flow: 0.8 ml/min

Diluent: ACN+$H_2O$

Purity: 93.65% r.t.=4.49 min, m/z=318.3[M+H]$^+$

1-Morpholin-4-yl-2-[4-(4,4,5,5-tetramethyl-[1,3,2]dioxaborolan-2-yl)-phenyl]-ethanone

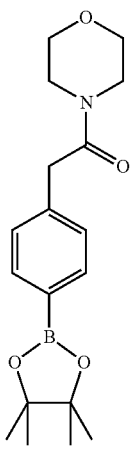 [SMILES: CC1(C)OB(c2ccc(CC(=O)N3CCOCC3)cc2)OC1(C)C]

To a solution of 2-(4-Iodo-phenyl)-1-morpholin-4-yl-ethanone (1.0 g, 3.02 mmol) and 4,4,5,5,4',4',5',5'-Octamethyl-[2,2']bi[[1,3,2]dioxaborolanyl](0.92 g, 3.62 mmol) in DMSO (20.0 mL) was added KOAc (0.74 mg, 7.55 mmol) at room temperature. N₂ was purged through the reaction mixture for 10 min. Pd(dppf)Cl₂.DCM (0.12 g, 0.15 mmol) was added and through the reaction mixture N₂ was purged for 10 min and stirred at 100° C. for 16 h. The reaction mixture was cooled to RT, diluted with EtOAc (50 mL) and washed with water (50 mL). The organic layer was washed with brine solution (50 mL), dried over anhydrous Na₂SO₄ and solvent was evaporated under reduced pressure. Crude compound was purified by column chromatography using 100-200 mesh silica gel and eluted with 40-50% EtOAc in pet-ether to afford 720 mg (yield: 72%) of the title compound as brown solid.

¹H NMR (DMSO-d6, 400 MHz, TMS) δ: 7.62-7.60 (2H, d), 7.24-7.22 (2H, d), 3.52 (2H, br, s), 3.47-3.45 (8H, br, m).

(3-Fluoro-4-(morpholine-4-carbonyl)phenyl) boronic acid

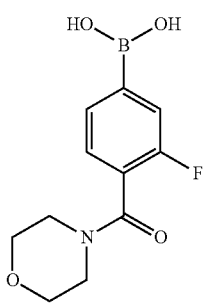 [SMILES: O=C(c1ccc(B(O)O)cc1F)N1CCOCC1]

To a solution of 4-borono-2-fluorobenzoic acid (1.0 g, 5.43 mmol) and HATU (2.0 g, 5.43 mmol) in DMF (20.0 mL) was added morpholine (0.9 g, 10.87 mmol) at room temperature. The reaction mixture was stirred at room temperature for 18 h. The reaction mixture was poured into ice cold water, acidified with 1N HCl, extracted with EtOAc (2×50 mL). The organic layer was washed with brine solution (20 mL), dried over anhydrous Na₂SO₄ and solvent was evaporated under reduced pressure to afford 1.2 g of crude compound as a colourless gum. Crude compound was directly used for the next step without any further purification.

4-(6-amino-5-(1-isopropyl-1H-1,2,3-triazol-4-yl)pyridin-3-yl)-2-methoxybenzoic acid

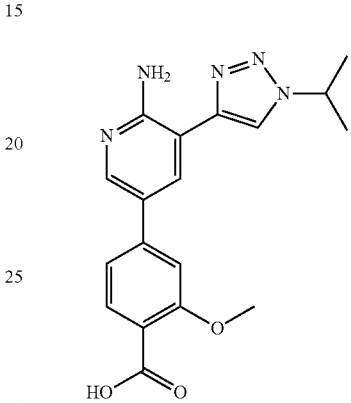

To a solution of 5-bromo-3-(1-isopropyl-1H-[1,2,3]triazol-4-yl)-pyridin-2-ylamine (300 mg, 1.06 mmol) and (3-methoxy-4-(methoxycarbonyl)phenyl)boronic acid (245 mg, 1.16 mmol) in 1,4-dioxane (10.0 mL)/water (5.0 mL) was added Cs₂CO₃ (1.0 g, 3.18 mmol) at room temperature. The reaction mixture was degassed with argon for 30 min. Then Pd(PPh₃)₄ (61 mg, 0.05 mmol) was added and allowed to stir at 120° C. for 30 min in CEM micro wave. The reaction mixture was cooled to RT, diluted with EtOAc (50 mL) and washed with water (50 mL). The aqueous layer was neutralized with 1N HCl, extracted with DCM (2×50 mL), washed with brine solution (20 mL), dried over anhydrous Na₂SO₄ and solvent was evaporated under reduced pressure. The crude compound was washed with diethyl ether to afford 260 mg (yield: 69.33%) of the title compound as pale yellow solid.

¹H NMR (DMSO-d₆, 400 MHz, TMS) δ: 12.50 (1H, s), 8.93 (1H, s), 8.44-8.43 (1H, d), 8.26-8.25 (1H, d), 7.74-7.72 (1H, d), 7.36-7.29 (2H, m), 7.24 (2H, s), 4.94-4.87 (1H, m), 3.93 (3H, s), 1.58 (3H, s), 1.57 (3H, s).

LCMS Conditions:
Column: BEH C18 (2.1×50 mm) 1.7μ
M-Phase A: 0.05% TFA in Water
M-Phase B: ACN
T/% B: 0/3, 0.3/3, 1/35, 2/98, 3.8/98, 3.9/3, 4/3
Flow: 0.6 ml/min
Diluent: ACN+H₂O
Purity: 87.26%
tR=1.24 min, m/z=354.48 [M+H]⁺

[5-[6-amino-5-(1-isopropyltriazol-4-yl)-3-pyridyl]-2-fluoro-phenyl]-morpholino-methanone

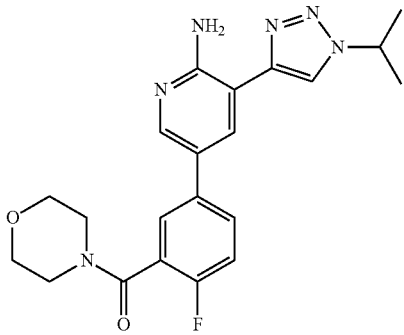 [SMILES: CC(C)n1cc(-c2cc(-c3ccc(F)c(C(=O)N4CCOCC4)c3)cnc2N)nn1]

To a solution of 5-bromo-3-(1-isopropyl-1H-[1,2,3]triazol-4-yl)-pyridin-2-ylamine (200 mg, 0.70 mmol) and (4-fluoro-3-(morpholine-4-carbonyl)phenyl)boronic acid (197 mg, 0.77 mmol) in 1,4-dioxane (10.0 mL)/water (5.0 mL) was added Cs$_2$CO$_3$ (690 mg, 2.12 mmol) at room temperature. The reaction mixture was degassed with argon for 30 min. Then Pd(PPh$_3$)$_4$ (40 mg, 0.035 mmol) was added and allowed to stir at 110° C. for 30 min in CEM micro wave. The reaction mixture was cooled to RT, diluted with EtOAc (50 mL) and washed with water (50 mL). The organic layer was washed with brine solution (20 mL), dried over anhydrous Na$_2$SO$_4$ and solvent was evaporated under reduced pressure. Crude compound was purified by column using 100-200 mesh silica gel. The column was eluted with 5% MeOH in DCM to afford 210 mg (yield: 72.41%) of title compound as pale yellow solid.

$^1$H NMR (DMSO-d$_6$, 400 MHz, TMS) δ: 8.93 (1H, s), 8.34-8.33 (1H, d), 8.21-8.20 (1H, d), 7.84-7.80 (1H, m), 7.73-7.70 (1H, m), 7.18 (2H, s), 7.39-7.35 (1H, t), 7.16 (2H, s), 4.91-4.88 (1H, m), 3.67 (4H, br), 3.56 (2H, br), 3.28 (2H, br), 1.58 (3H, s), 1.56 (3H, s).

LCMS Conditions:
Column: XBRIDGE-C18(4.6×75 mm) 3.5μ
M-Phase A: 0.1% HCOOH(Aq)
M-Phase B: 0.1% HCOOH in(ACN)
T/% B: 0/5, 0.5/5, 2/98, 8/98, 8.1/5
Flow: 1.0 ml/min
Diluent: ACN+H$_2$O
Purity: 98.61%
tR=1.67 min, m/z=411.2 [M+H]$^+$

4-(6-amino-5-(1-isopropyl-1H-1,2,3-triazol-4-yl) pyridin-3-yl)-2-methylbenzoic acid

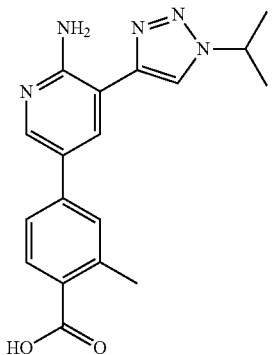 [SMILES: Cc1cc(-c2cnc(N)c(-c3cn(C(C)C)nn3)c2)ccc1C(=O)O]

Cs$_2$CO$_3$ (1.03 g, 3.18 mmol) was added to a solution of 5-bromo-3-(1-isopropyl-1H-[1,2,3]triazol-4-yl)-pyridin-2-ylamine (300 mg, 1.06 mmol) and (4-(methoxycarbonyl)-3-methylphenyl)boronic acid (247 mg, 1.27 mmol) in dioxane:water (10 mL: 5 mL), degassed the reaction mixture for 10 min with nitrogen. Then added Pd(PPh$_3$)$_4$ (61 mg, 0.053 mmol), degassed the reaction mixture for additional 10 min with nitrogen, the reaction mixture was heated to 120° C. in microwave for 1 h. LiOH (222 mg, 5.30 mmol) was added to the reaction mixture and, heated to 100° C. for 3 h. Then diluted with water (50 mL) and extracted with ethyl acetate (2×30 mL). Aqueous layer was acidified with 2N HCl, pH was adjusted to 6 and extracted with ethyl acetate (2×30 mL). Dried over Na$_2$SO$_4$ and concentrated under reduced pressure to afford 210 mg of (Yield: 58.65%) the title compound as a white solid.

$^1$HNMR (DMSO-d$_6$, 400 MHz, TMS) δ: 8.95 (1H, s), 8.40-8.39 (1H, d), 8.26 (1H, d), 7.89-7.87 (1H, d), 7.63-7.60 (2H, m), 7.22 (2H, br, s), 4.94-4.87 (1H, m), 2.60 (3H, s), 1.58-1.56 (6H, d, J=6.8 Hz).

LCMS Conditions:
Column: BEH C18 (2.1×50 mm) 1.7μ
M-Phase A: 0.1% HCOOH 1N H$_2$O
M-Phase B: ACN
T/% B: 0.0/3, 0.2/3, 1/35, 2/98, 3.85/98, 3.9/3, 4/3
Flow: 0.6 ml/min
Diluents: ACN+H$_2$O
Purity: 95.76%
tR=1.17 min, m/z=338.2[M+H]$^+$

Compounds of the Invention

1: 5-(1H-Indol-5-yl)-3-(5-isopropyl-[1,3,4]oxadiazol-2-yl)-pyridin-2-ylamine

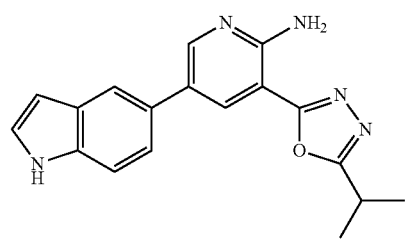 [SMILES: CC(C)c1nnc(-c2cc(-c3ccc4[nH]ccc4c3)cnc2N)o1]

To a solution of 5-bromo-3-(5-isopropyl-[1,3,4]oxadiazol-2-yl)-pyridin-2-ylamine (250 mg, 0.883 mmol) in dioxane (15 mL) and water (7 mL) were added K$_2$CO$_3$ (365 mg, 2.649 mmol), indole-5-boronic acid (156 mg, 0.971 mmol) in a sealed tube. The reaction mixture was degassed by N$_2$ for 20 min, then Pd(PPh$_3$)$_4$ (102 mg, 0.088 mmol) was added and stirred for 18 h at 100° C. Water (20 mL) was added and extracted with ethyl acetate (3×20 mL) and the organic layer was washed with brine, dried over anhydrous sodium sulphate, and concentrated under reduced pressure. Crude product was purified by column chromatography using 100-200 mesh silica gel compound eluted with 40% ethyl acetate in petroleum ether to afford the title compound as a yellow solid.

Yield: 200 mg, (71.1%)

$^1$HNMR (DMSO-d$_6$, 400 MHz, TMS) δ: 11.14 (1H, br s), 8.55-8.54 (1H, d), 8.25-8.24 (1H, d), 7.81 (1H, s), 7.49-7.47 (1H, d), 7.39-7.27 (4H, m), 6.49 (1H, s), 3.35-3.28 (1H, m), 1.41-1.39 (6H, d).

LC-MS: m/z=320.0 (MH$^+$), t$_R$=0.53, method B.

2: 3-(5-Cyclopropyl-[1,3,4]oxadiazol-2-yl)-5-(1H-indol-5-yl)-pyridin-2-ylamine

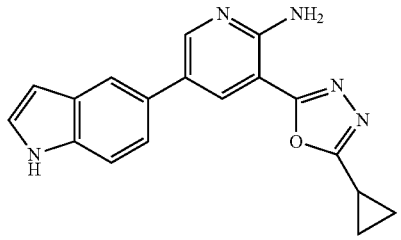 [SMILES: Nc1ncc(-c2ccc3[nH]ccc3c2)cc1-c1nnc(C2CC2)o1]

5-Bromo-3-(5-cyclopropyl-[1,3,4]oxadiazol-2-yl)-pyridin-2-ylamine (200 mg, 0.71 mmol), 5-indolyl boronic acid (112 mg, 0.78 mmol), $K_2CO_3$ (290 mg, 2.13 mmol), 1,4-dioxane (10.0 mL) and water (4.0 mL) were taken in a sealed tube and degassed with nitrogen for 15 min. Then Pd(PPh$_3$)$_4$ (41 mg, 0.03 mmol) was added and stirred for 18 h at 100° C. The reaction mixture was diluted with ice-cold water and extracted with EtOAc. The combined extracts were dried over $Na_2SO_4$ and evaporated under reduced pressure to get crude 3-(5-cyclopropyl-[1,3,4]oxadiazol-2-yl)-5-(1H-indol-5-yl)-pyridin-2-ylamine. Crude compound was purified by column chromatography using silica gel (100-200 mesh). The column was eluted with 30% EtOAc in petroleum ether to afford the title compound as a pale yellow solid.

Yield: 28 mg (21%)

$^1$H NMR (DMSO-d$_6$, 400 MHz, TMS) δ: 11.13 (s, 1H), 8.53-8.52 (d), 8.21-8.20 (d, 1H), 7.80 (s, 1H), 7.48-7.46 (d, 1H), 7.38-7.36 (m, 2H), 7.24-7.23 (broad s, 2H, NH$_2$), 6.48 (s, 1H), 2.38-2.31 (m, 1H), 1.20-1.18 (m, 4H).

LC-MS: m/z=318.2 (MH$^+$), t$_R$=0.49, method B.

3: 3-(5-Cyclopropyl-[1,3,4]oxadiazol-2-yl)-5-(1-methyl-2,3-dihydro-1H-indol-5-yl)-pyridin-2-ylamine

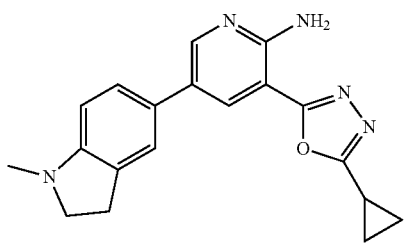 [SMILES: CN1CCc2cc(-c3cnc(N)c(-c4nnc(C5CC5)o4)c3)ccc21]

To a solution of 3-(5-cyclopropyl-[1,3,4]oxadiazol-2-yl)-5-(1-methyl-1H-indol-5-yl)-pyridin-2-ylamine (160 mg, 0.48 mmol) in TFA at 0° C. was added triethylsilane (0.2 mL, 1.20 mmol) drop-wise over a period of 5 min, and stirred for 2 h at 0° C. The reaction mixture was diluted with water (20 mL) and neutralized with saturated aqueous NaHCO$_3$ solution and extracted with ethyl acetate (3×20 mL). The organic layer was washed with brine, dried over anhydrous sodium sulphate and concentrated under reduced pressure to get crude product. The crude product was purified by column chromatography using 100-200 mesh silica gel and compound was eluted with 40% ethyl acetate in petroleum ether to afford the title compound.

Yield: 80 mg (Yield: 50%)

$^1$HNMR (DMSO-d$_6$, 400 MHz, TMS) δ: 8.42-8.41 (1H, d), 8.09-8.08 (1H, d), 7.35 (1H, s), 7.32-7.30 (1H, d), 7.20-7.18 (2H, broad s, NH$_2$), 6.58-6.56 (1H, d), 3.31-3.26 (2H, t), 2.95-2.91 (2H, t), 2.73 (3H, s), 2.36-2.30 (1H, m), 1.19-1.17 (4H, m).

4: 3-[5-(1-Methyl-piperidin-4-yl)-[1,3,4]oxadiazol-2-yl]-5-p-tolyl-pyridin-2-ylamine

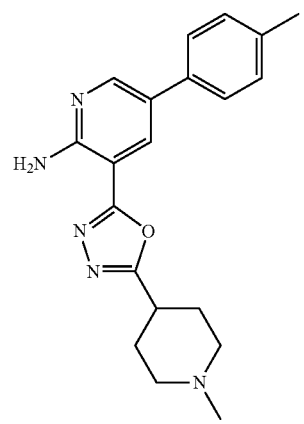 [SMILES: Cc1ccc(-c2cnc(N)c(-c3nnc(C4CCN(C)CC4)o3)c2)cc1]

To a solution of 3-(5-piperidin-4-yl-[1,3,4]oxadiazol-2-yl)-5-p-tolyl-pyridin-2-ylamine (250 mg, 0.746 mmol) in THF (25 mL) was added NaH (55%) (48.8 mg, 1.119 mmol) at 0° C. The reaction mixture was stirred at 0° C. for 1 h. Then MeI (95 mg, 0.671 mmol) was added at 0° C., and the reaction mixture was stirred at 0° C. for a further 3 h. The reaction mixture was then poured into ice-water (30 mL) and extracted with ethyl acetate (3×20 mL). The organic layer was washed with brine, dried over anhydrous sodium sulphate and concentrated under reduced pressure to afford crude compound. Crude compound was purified by preparative HPLC to afford the title compound as a pale yellow solid.

Yield: 15 mg (5.7%).

Preparative HPLC Conditions:

Column: X-BRIDGEC8 (250×20 mm) 5.0 μm

Mobile phase A: 0.01M Ammonium Acetate

Mobile phase B: ACN:MeOH (1:1)

Time (min)/% B: 0/30, 5/50, 10/50, 15/100

Flow: 15 mL/min

Solubility: MeOH+THF

Loading: 20 mg/injection

Column Temp ° C.: Ambient $^1$HNMR (DMSO-d$_6$, 400 MHz, TMS) δ: 8.54-8.53 (1H, d), 8.25-8.24 (1H, d), 7.59-7.57 (2H, d), 7.37 (2H, br, s), 7.28-7.26 (2H, d), 3.03 (1H, m), 2.83-2.67 (2H, m), 2.49 (3H, s), 2.34 (3H, br, s), 2.23-2.08 (4H, m), 1.86-1.83 (2H, m).

LC-MS: m/z=350.2 (MH$^+$), t$_R$=0.4, method B.

5: 5-(1-Methyl-2,3-dihydro-1H-indol-5-yl)-3-(5-piperidin-4-yl-[1,3,4]oxadiazol-2-yl)-pyridin-2-ylamine

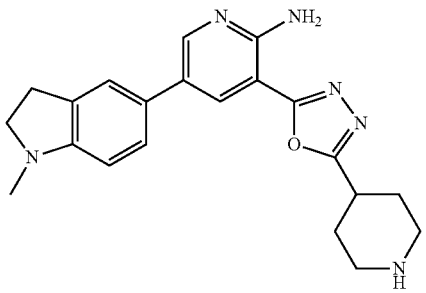 [SMILES: CN1CCc2cc(-c3cnc(N)c(-c4nnc(C5CCNCC5)o4)c3)ccc21]

To a solution of 4-{5-[2-amino-5-(1-methyl-1H-indol-5-yl)-pyridin-3-yl]-[1,3,4]oxadiazol-2-yl}-piperidine-1-carboxylic acid tert-butyl ester (300 mg, 0.63 mmol) in TFA (2.0 mL) at 0° C. was added triethylsilane (146 mg, 1.26 mmol) drop-wise over a period of 5 min, and stirred for 2 h at 0° C. The reaction was diluted with water (20 mL), neutralized with saturated aqueous NaHCO$_3$ solution and extracted with ethyl acetate (3×20 mL). The organic layer was washed with brine, dried over anhydrous sodium sulphate and concentrated under reduced pressure to obtain crude product. Crude product was purified by washing with diethyl ether and hexane to afford the title compound as a yellow solid:

Yield: 150 mg (63.2%)

$^1$HNMR (DMSO-d$_6$, 400 MHz, TMS) δ: 8.44-8.43 (1H, d), 8.12-8.11 (1H, d), 7.35 (1H, s), 7.32-7.30 (1H, d), 7.24-7.22 (2H, broad s), 6.58-6.56 (1H, d), 3.31-3.26 (2H, m), 3.17-3.11 (1H, m), 3.04-3.01 (2H, d), 2.96-2.91 (2H, t), 2.73 (3H, s), 2.67-2.61 (2H, t), 2.03-2.00 (2H, d), 1.75-1.65 (2H, m).

6: 3-(5-Cyclopropyl-[1,3,4]oxadiazol-2-yl)-5-(4-morpholin-4-ylmethyl-phenyl)-pyridin-2-ylamine

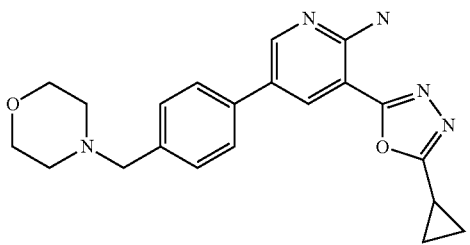 [SMILES: Nc1ncc(-c2ccc(CN3CCOCC3)cc2)cc1-c1nnc(C2CC2)o1]

To a solution of 5-bromo-3-(5-cyclopropyl-[1,3,4]oxadiazol-2-yl)-pyridin-2-ylamine (300 mg, 1.06 mmol) in dioxane (10 mL) and water (6 mL) were added K$_2$CO$_3$ (438 mg, 3.18 mmol), 4-(morpholinomethyl)-boronic acid (259 g, 1.17 mmol) in a sealed tube. The reaction mixture was degassed with argon for 20 min and then Pd(PPh$_3$)$_4$ (61.2 mg, 0.05 mmol) was added to the reaction mixture. The reaction mixture was stirred for 18 h at 100° C. The reaction was diluted with water (50 mL) extracted with ethyl acetate (2×50 mL) and organic layer was washed with brine, dried over anhydrous sodium sulphate and concentrated under reduced pressure to get crude product, which was purified by column chromatography using 100-200 mesh silica gel compound eluted with ethyl acetate to afford 120 mg of the crude product. This was further purified by washing with 20% chloroform in hexane to afford the title compound as a brown solid.

Yield: 28 mg (6.9%)

$^1$HNMR (DMSO-d$_6$, 400 MHz, TMS) δ: 8.53-8.52 (1H, s), 8.22-8.21 (1H, s), 7.64-7.62 (2H, d), 7.40-7.35 (4H, m), 3.60-3.56 (4H, m), 3.50-3.49 (2H, m), 2.37-2.30 (5H, m), 1.20-1.18 (4H, d).

LC-MS: m/z=378.2 (MH$^+$), t$_R$=0.32, method A.

7: 5-(3-Methoxy-phenyl)-3-(5-piperidin-4-yl-[1,3,4]oxadiazol-2-yl)-pyridin-2-ylamine

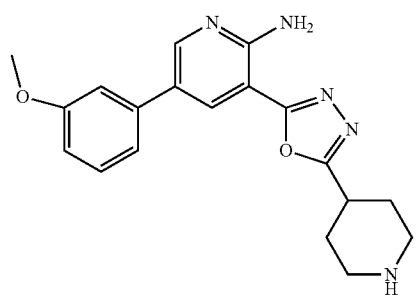 [SMILES: COc1cccc(-c2cnc(N)c(-c3nnc(C4CCNCC4)o3)c2)c1]

To a solution of 4-{5-[2-amino-5-(3-methoxy-phenyl)-pyridin-3-yl]-[1,3,4]oxadiazol-2-yl}-piperidine-1-carboxylic acid tert-butyl ester (200 mg, 0.44 mmol) in chloroform (10 mL) was added 2M HCl in diethyl ether (10 mL) at 0° C., and the reaction mixture was stirred for 4 h at 0° C. After completion of the reaction, solvents in reaction mixture were evaporated under vacuum to get crude product. Crude product was purified by washing with ethyl acetate and hexane to afford the title compound as a pale yellow powder.

Yield: 130 mg (75.0%)

$^1$HNMR (DMSO-d$_6$, 400 MHz, TMS) δ: 9.02-8.98 (1H, broad s), 8.78-8.74 (1H, broad s), 8.62-8.61 (1H, d), 8.36-8.35 (1H, d), 7.42-7.38 (1H, t), 7.26-7.23 (2H, m), 6.96-6.94 (1H, dd), 3.83 (3H, s), 3.49-3.43 (1H, m), 3.43-3.36 (2H, d), 3.13-3.04 (2H, m), 2.33-2.28 (2H, dd), 2.09-1.99 (2H, m).

LC-MS: m/z=352.15 (MH$^+$), t$_R$=0.34, method A.

8: 5-(3-Methoxy-phenyl)-3-[5-(1-methyl-piperidin-4-yl)-[1,3,4]oxadiazol-2-yl]-pyridin-2-ylamine

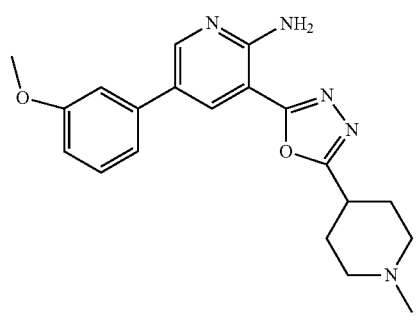

To a solution of 5-(3-methoxyphenyl)-3-[5-(4-piperidyl)-1,3,4-oxadiazol-2-yl]pyridin-2-amine (150 mg, 0.42 mmol) in THF (20 mL) was added 60% NaH (25.0 mg, 064 mmol) at 0° C. and the reaction mixture was stirred at 0° C. for 10 min. Then MeI (54.5 mg, 0.38 mmol) was added at 0° C. and stirred the reaction mixture at 0° C. for 2 h. The reaction mixture was poured into ice-water (30 mL), extracted with ethyl acetate (3×20 mL), organic layer was washed with brine, dried over anhydrous sodium sulphate and concentrated under reduced pressure. Crude product was purified by preparative TLC to afford the title compound as a yellow solid.

Yield: 30 mg (Yield: 19.3%)

$^1$HNMR (DMSO-d$_6$, 400 MHz, TMS) δ: 8.59-8.58 (1H, d), 8.27-8.26 (1H, d), 7.42-7.36 (3H, m), 7.24-7.20 (2H, m), 6.94-6.91 (1H, dd), 3.83 (3H, s), 3.45-3.36 (3H, m), 3.11-2.96 (2H, m), 2.70 (3H, s), 2.35-2.28 (2H, m), 2.16-1.98 (2H, m).

LC-MS: m/z=366.1 (MH$^+$), t$_R$=0.35, method A.

9: 3-(1-Isopropyl-1H-[1,2,3]triazol-4-yl)-5-(1-methyl-1H-indol-5-yl)-pyridin-2-ylamine

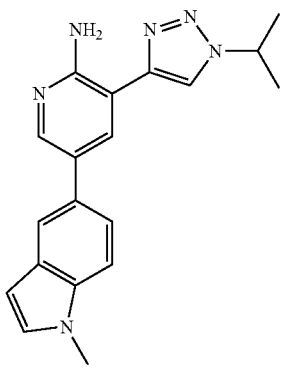 [SMILES: CC(C)n1cc(-c2cc(-c3ccc4c(ccn4C)c3)cnc2N)nn1]

To a solution of 5-bromo-3-(1-isopropyl-1H-[1,2,3]triazol-4-yl)-pyridin-2-ylamine (200 mg, 0.708 mmol) and N-methylindole-5-boronic acid (124 mg, 0.708 mmol) in 1,4-dioxane (6.0 mL)/water (3.0 mL) was added K$_2$CO$_3$ (293 mg, 2.126 mmol) at room temperature. The reaction mixture was purged with argon for 30 min. Then Pd(PPh3)$_4$ (41 mg, 0.035 mmol) was added and the mixture was allowed to stir at 100° C. for 16 h. The reaction mixture was cooled to RT, diluted with EtOAc (20 mL) and washed with water (20 mL). The organic layer was washed with brine solution (20 mL), dried over anhydrous Na$_2$SO$_4$ and solvent was evaporated under reduced pressure to afford crude compound. Crude compound was purified by column using 100-200 mesh silica gel. The column was eluted with 80% EtOAc in Pet. Ether to afford the title compound as pale yellow solid.

Yield: 160 mg (69.5%)

$^1$H NMR (DMSO-d$_6$, 400 MHz, TMS) δ: 8.96 (1H, s), 8.31-8.30 (1H, d), 8.21-8.20 (1H, d), 7.82 (1H, s), 7.51-7.45 (2H, m), 7.34-7.33 (1H, d), 6.96 (2H, br), 6.46-6.45 (1H, d), 4.94-4.85 (1H, m), 1.58 (3H, s), 1.56 (3H, s).

LC-MS: m/z=333.15 (MH$^+$), t$_R$=0.57, method A.

10: 3-(1-Isopropyl-1H-[1,2,3]triazol-4-yl)-5-(1-methyl-2,3-dihydro-1H-indol-5-yl)-pyridin-2-ylamine

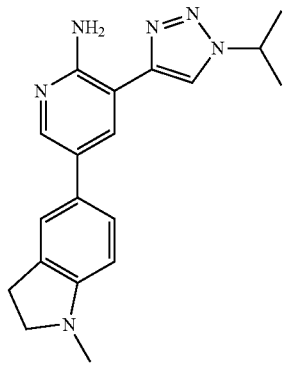 [SMILES: CC(C)n1cc(-c2cc(-c3ccc4c(c3)CCN4C)cnc2N)nn1]

To a solution of 3-(1-isopropyltriazol-4-yl)-5-(1-methylindol-5-yl)pyridin-2-amine (170 mg, 0.511 mmol) in TFA (5.0 mL) was added triethylsilane (0.16 mL, 1.022 mmol) at 0° C. The reaction temperature was stirred for 1 h at 0° C. The reaction mixture was poured into ice-cold water (20 mL), basified with saturated NaHCO$_3$, extracted with EtOAc (30 mL), dried over anhydrous Na$_2$SO$_4$ and evaporated the solvent under reduced pressure to get crude compound. Crude compound was washed with diethyl ether to afford title compound as a yellow solid.

Yield: 80 mg (yield: 46.7%)

$^1$H NMR (DMSO-d$_6$, 400 MHz, TMS) δ: 8.91 (1H, s), 8.19 (1H, s), 8.08 (1H, s), 7.37 (1H, s), 7.33-7.31 (1H, d), 6.91 (2H, br), 6.57-6.55 (1H, d), 4.92-4.85 (1H, m), 3.31-3.26 (2H, m), 2.94-2.91 (2H, t), 2.72 (3H, s), 1.57 (3H, s), 1.56 (3H, s).

LC-MS: m/z=335 (MH$^+$), t$_R$=0.48, method A.

11: 3-(1-Isopropyl-1H-[1,2,3]triazol-4-yl)-5-(1-methyl-2,3-dihydro-1H-indol-5-yl)-pyrazin-2-ylamine

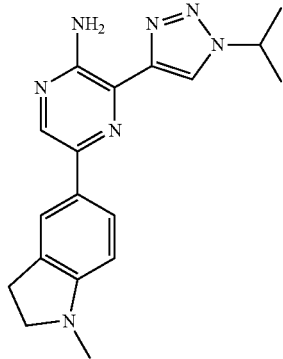 [SMILES: CC(C)n1cc(-c2nc(-c3ccc4c(c3)CCN4C)cnc2N)nn1]

To a solution of 3-(1-isopropyl-1H-[1,2,3]triazol-4-yl)-5-(1-methyl-1H-indol-5-yl)-pyrazin-2-ylamine (200 mg, 0.60 mmol) in TFA (10.0 mL) was added triethylsilane (0.19 mL, 1.20 mmol) at 0° C. The reaction temperature was stirred for 2 h at 0° C. The reaction mixture was poured into ice-cold water (20 mL), basified with saturated NaHCO₃, extracted with EtOAc (30 mL), dried over anhydrous Na₂SO₄ and evaporated the solvent under reduced pressure to get crude compound. Crude compound was washed with diethyl ether to afford the title compound as a brown solid.

Yield: 125 mg (62.1%)

¹HNMR (DMSO-d₆, 400 MHz, TMS) δ: 8.88 (1H, s), 8.45 (1H, s), 7.78-7.45 (2H, m), 7.22 (2H, br), 6.56-6.54 (1H, d), 5.00-4.93 (1H, m), 3.32-3.29 (2H, m), 2.97-2.93 (2H, t), 2.75 (3H, s), 1.60-1.58 (1H, d).

12: 3-(1-Isopropyl-H-[1,2,3]triazol-4-yl)-5-(4-morpholin-4-ylmethyl-phenyl)-pyridin-2-ylamine

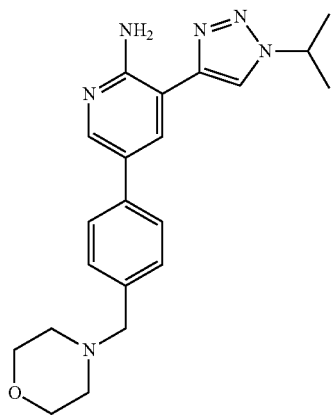 [SMILES: CC(C)n1cc(-c2cc(-c3ccc(CN4CCOCC4)cc3)cnc2N)nn1]

To a solution of 5-bromo-3-(1-isopropyl-1H-[1,2,3]triazol-4-yl)-pyridin-2-ylamine (500 mg, 1.77 mmol) and 4-[4-(4,4,5,5-tetramethyl-[1,3,2]dioxaborolan-2-yl)-benzyl]-morpholine (537 mg, 1.77 mmol) in ethylene glycol dimethyl ether (6.0 mL)/water (4.0 mL) was added Cs₂CO₃ (1.15 g, 3.54 mmol) at room temperature. The reaction mixture was purged with argon for 30 min. Then Pd(dppf)Cl₂.DCM (72.2 mg, 0.08 mmol) was added and allowed to stir at 140° C. for 6 h in microwave. After 6 h, the reaction mixture was cooled to RT, diluted with EtOAc (50 mL) and washed with water (50 mL). The organic layer was washed with brine solution (50 mL), dried over anhydrous Na₂SO₄ and solvent was evaporated under reduced pressure to afford crude product. The crude compound was purified by column using 100-200 mesh silica gel. The column was eluted with 5-95% MeOH in DCM to afford the title compound as a brown solid.

Yield: 72 mg (10.7%)

¹H NMR (DMSO-d₆, 400 MHz, TMS) δ: 8.94 (1H, s), 8.31 (1H, s), 8.20 (1H, d), 7.65-7.63 (2H, d), 7.38-7.36 (2H, d), 7.10 (2H, br s), 4.93-4.86 (1H, m), 3.58 (4H, s), 3.49 (2H, s), 2.37 (4H, m), 1.57-1.56 (6H, d).

LC-MS: m/z=379.1 (MH⁺), $t_R$=0.3, method A.

13: 3-(1-Isopropyl-1H-[1,2,3]triazol-4-yl)-5-(4-morpholin-4-yl-phenyl)-pyridin-2-ylamine

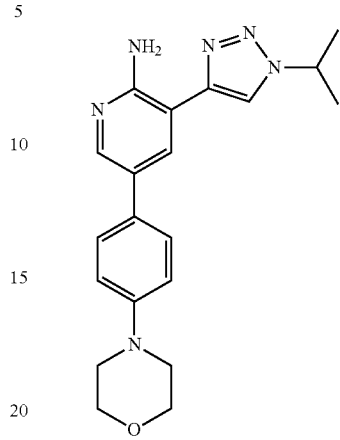

To a solution of 5-bromo-3-(1-isopropyl-1H-[1,2,3]triazol-4-yl)-pyridin-2-ylamine (100 mg, 0.35 mmol) and 4-[4-(4,4,5,5-tetramethyl-[1,3,2]dioxaborolan-2-yl)-phenyl]-morpholine (88 mg, 0.42 mmol) in 1,4-dioxane (7.0 mL)/water (3.0 mL) was added Cs₂CO₃ (227 mg, 0.70 mmol) at room temperature. The reaction mixture was purged with argon for 30 min. Then Pd(PPh₃)₄ (20.2 mg, 0.017 mmol) was added and allowed to stir at 100° C. for 16 h. The reaction mixture was cooled to RT, diluted with EtOAc (50 mL) and washed with water (50 mL). The organic layer was washed with brine solution (50 mL), dried over anhydrous Na₂SO₄ and solvent was evaporated under reduced pressure to afford crude compound. Crude compound was purified by column using 100-200 mesh silica gel. The column was eluted with 3-97% MeOH in DCM to afford the title compound as a yellow solid.

Yield: 45 mg (34.8%)

¹H NMR (DMSO-d₆, 400 MHz, TMS) δ: 8.92 (1H, s), 8.25 (1H, d), 8.13 (1H, d), 7.57-7.54 (2H, d), 7.02-7.00 (2H, d), 6.97 (2H, br s), 4.92-4.85 (1H, m), 3.77-3.74 (4H, t), 3.15-3.12 (4H, t), 1.57-1.56 (6H, d).

LC-MS: m/z=365.2 (MH⁺), $t_R$=0.47, method A.

14: 3-(1-Isopropyl-1H-[1,2,3]triazol-4-yl)-5-[4-(2-morpholin-4-yl-ethyl)-phenyl]-pyridin-2-ylamine

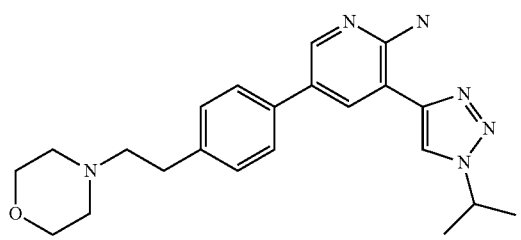 [SMILES: CC(C)n1cc(-c2cc(-c3ccc(CCN4CCOCC4)cc3)cnc2N)nn1]

To a solution of 4-{2-[4-(4,4,5,5-tetramethyl-[1,3,2]dioxaborolan-2-yl)-phenyl]-ethyl}-morpholine (can be prepared as described in US2002026052) (101 mg, 0.31 mmol) and 5-bromo-3-(1-isopropyl-1H-[1,2,3]triazol-4-yl)-pyridin-2-ylamine (90 mg, 0.31 mmol) in 1,4-dioxane (7.0 mL)/water (3.0 mL) was added Cs₂CO₃ (251 mg, 0.70 mmol) at RT. N₂ was purged through the reaction mixture for 10 min.

Pd(PPh$_3$)$_4$ (18 mg, 0.015 mmol) was added and through the reaction mixture N$_2$ was purged for 10 min and stirred at 100° C. for 16 h. The reaction mixture was cooled to RT, diluted with EtOAc (50 mL) and washed with water (50 mL). The organic layer was washed with brine solution (50 mL), dried over anhydrous Na$_2$SO$_4$ and solvent was evaporated under reduced pressure to afford crude compound (GVK-B1319-120A1). Crude compound was purified by column using 100-200 mesh silica gel and eluted with 2-3% MeOH in DCM to afford 65 mg of a brown semisolid. Further purification of Prep-HPLC furnished 14 mg of the title compound as an off-white solid.

$^1$H NMR (DMSO-d$_6$, 400 MHz, TMS) δ: 8.93 (1H, s), 8.29 (1H, d), 8.18 (1H, d), 7.60-7.58 (2H, d), 7.31-7.29 (2H, d), 7.06 (2H, br s), 4.92-4.86 (1H, m), 3.58 (4H, s), 2.78-2.75 (2H, t), 2.44 (6H, br, s), 1.57-1.56 (6H, d).

LC-MS: m/z=393.2 (MH$^+$), t$_R$=0.32, method A.

15: 5-(3-fluoro-4-(morpholinomethyl)phenyl)-3-(1-isopropyl-1H-1,2,3-triazol-4-yl)pyridin-2-amine

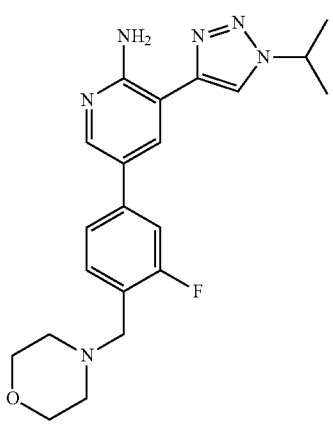 [SMILES: CC(C)n1cc(-c2cc(-c3ccc(CN4CCOCC4)c(F)c3)cnc2N)nn1]

To a solution of 5-bromo-3-(1-isopropyl-1H-[1,2,3]triazol-4-yl)-pyridin-2-ylamine (200 mg, 0.70 mmol) and 4-(2-fluoro-4-(4,4,5,5-tetramethyl-1,3,2-dioxaborolan-2-yl)benzyl)morpholine (250 mg, 0.77 mmol) in 1,4-dioxane (10.0 mL)/water (5.0 mL) was added Cs$_2$CO$_3$ (690 mg, 2.12 mmol) at room temperature. The reaction mixture was degassed with argon for 30 min. Then Pd(PPh$_3$)$_4$ (40 mg, 0.03 mmol) was added and allowed to stir at 110° C. for 30 min in CEM micro wave. The reaction mixture was cooled to RT, diluted with EtOAc (50 mL) and washed with water (50 mL). The organic layer was washed with brine solution (20 mL), dried over anhydrous Na$_2$SO$_4$ and solvent was evaporated under reduced pressure. The crude compound was purified by column using 100-200 mesh silica gel. The column was eluted with 80% EtOAc in hexanes to afford 100 mg (yield: 35.71%) of the title compound as pale yellow solid.

$^1$H NMR (DMSO-d$_6$, 400 MHz, TMS) δ: 8.95 (1H, s), 8.37-8.36 (1H, d), 8.24-8.23 (1H, d), 7.55-7.52 (2H, m), 7.46-7.42 (1H, t), 7.19 (2H, s), 4.93-4.86 (1H, m), 3.58-3.56 (4H, m), 3.54 (2H, s), 2.40 (4H, br), 1.58 (3H, s), 1.56 (3H, s).

LC-MS: m/z=397.5 (MH$^+$), t$_R$=0.33, method A.

16: (4-(6-amino-5-(1-isopropyl-1H-1,2,3-triazol-4-yl)pyridin-3-yl)-2-fluorophenyl)(morpholino)methanone

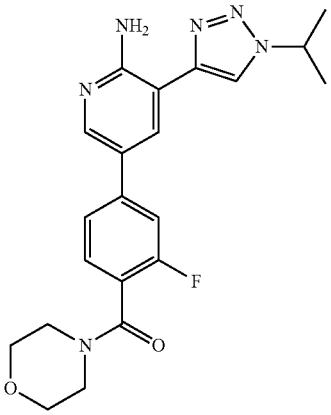

To a solution of (3-fluoro-4-(morpholine-4-carbonyl)phenyl)boronic acid (269 mg, 1.06 mmol) and of 5-bromo-3-(1-isopropyl-1H-[1,2,3]triazol-4-yl)-pyridin-2-ylamine (250 mg, 0.886 mmol) in 1,4-dioxane (10.0 mL)/water (5.0 mL) was added Cs$_2$CO$_3$ (863 mg, 2.65 mmol) at room temperature. The reaction mixture was degassed with argon for 30 min. Then Pd(PPh$_3$)$_4$ (51 mg, 0.04 mmol) was added and allowed to stir at 120° C. for 30 min in CEM micro wave. The reaction mixture was cooled to RT, diluted with EtOAc (50 mL) and washed with water (50 mL). The organic layer was washed with brine solution (20 mL), dried over anhydrous Na$_2$SO$_4$ and solvent was evaporated under reduced pressure to afford crude compound. Crude compound was purified by column using 100-200 mesh silica gel. The column was eluted with 5% MeOH in DCM to afford 125 mg (yield: 34.43%) of the title compound as pale yellow solid.

$^1$H NMR (DMSO-d$_6$, 400 MHz, TMS) δ: 8.96 (1H, s), 8.43-8.42 (1H, d), 8.296-8.29 (1H, d), 7.70-7.64 (2H, m), 7.49-7.45 (1H, t), 7.28 (2H, s), 4.92-4.89 (1H, m), 3.66 (4H, br), 3.55 (2H, br), 3.29 (2H, br), 1.58 (3H, s), 1.57 (3H, s).

LC-MS: m/z=411.1 (MH$^+$), t$_R$=0.41, method A.

17: [4-[6-amino-5-(1-isopropyltriazol-4-yl)-3-pyridyl]-2-methoxy-phenyl]-morpholino-methanone

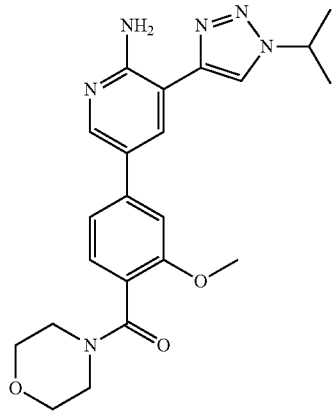

To a solution of 4-(6-amino-5-(1-isopropyl-1H-1,2,3-triazol-4-yl)pyridin-3-yl)-2-methoxybenzoic acid (260 mg, 0.735 mmol) and HATU (418 mg, 1.10 mmol) in DMF (10.0 mL) were added morpholine (77 mg, 0.88 mmol) and DIPEA (0.4 mL, 2.205 mmol) at room temperature. The reaction mixture was stirred at room temperature for 18 h. The reaction mixture was poured into ice cold water, extracted with EtOAc (100 mL). The organic layer was washed with brine solution (50 mL), dried over anhydrous $Na_2SO_4$ and solvent was evaporated under reduced pressure. Crude compound was purified by column using 100-200 mesh silica gel. The column was eluted with 100% EtOAc to afford 250 mg (yield: 80.64%) of the title compound as pale yellow solid.

$^1$H NMR (DMSO-$d_6$, 400 MHz, TMS) δ: 8.91 (1H, s), 8.39-8.38 (1H, d, J=2.4 Hz), 8.226-8.22 (1H, d, J=2.4 Hz), 7.32-7.30 (2H, m), 7.26-7.24 (1H, m), 7.12 (2H, s), 4.93-4.87 (1H, m), 3.91 (3H, s), 3.63 (4H, br), 3.52 (2H, br), 3.17-3.16 (2H, br), 1.58 (3H, s), 1.56 (3H, s).

LC-MS: m/z=423.1 (MH$^+$), $t_R$=0.41, method A.

18: 3-(1-isopropyltriazol-4-yl)-5-[3-methoxy-4-(morpholinomethyl)phenyl]pyridin-2-amine

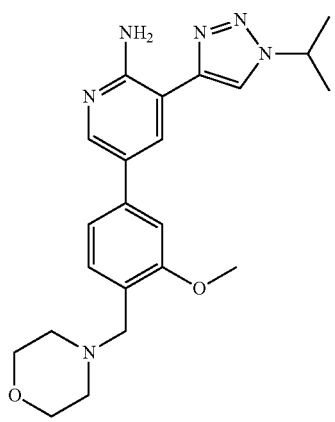 [SMILES: COc1cc(-c2cnc(N)c(-c3cn(C(C)C)nn3)c2)ccc1CN1CCOCC1]

To a solution of [4-[6-amino-5-(1-isopropyltriazol-4-yl)-3-pyridyl]-2-methoxy-phenyl]-morpholino-methanone (200 mg, 0.473 mmol) in THF (10.0 mL) was added $BF_3.Et_2O$ (0.3 mL, 2.36 mmol) at 0° C. and stirred for 30 min. After 30 min, $NaBH_4$ (89 mg, 2.36 mmol) was added at 0° C. and stirred at room temperature for 18 h. After cooling to 0° C., quenched with MeOH (2 mL) and heated to reflux for 6 h. The reaction mixture was diluted with EtOAc (50 mL), washed with water (30 mL), dried over anhydrous $Na_2SO_4$ and solvent was evaporated under reduced pressure. Crude compound was purified by column using 100-200 mesh silica gel. The column was eluted with 100% EtOAc to afford 100 mg (yield: 51.81%) of the title compound as white solid.

$^1$H NMR (DMSO-$d_6$, 400 MHz, TMS) δ: 8.90 (1H, s), 8.34-8.33 (1H, d), 8.18-8.17 (1H, d), 7.36-7.34 (1H, d), 7.22-7.21 (2H, m), 7.08 (2H, s), 4.91-4.88 (1H, m), 3.88 (3H, s), 3.59-3.57 (4H, m), 3.48 (2H, s), 2.39 (4H, br), 1.58 (3H, s), 1.56 (3H, s).

LC-MS: m/z=409.1 (MH$^+$), $t_R$=0.33, method A.

19: 5-[4-fluoro-3-(morpholinomethyl)phenyl]-3-(1-isopropyltriazol-4-yl)pyridin-2-amine

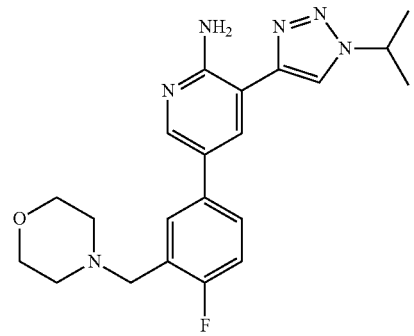 [SMILES: CC(C)n1cc(-c2cc(-c3ccc(F)c(CN4CCOCC4)c3)cnc2N)nn1]

To a solution of [5-[6-amino-5-(1-isopropyltriazol-4-yl)-3-pyridyl]-2-fluoro-phenyl]-morpholino-methanone (150 mg, 0.365 mmol) in THF (10.0 mL) was added $BF_3.Et_2O$ (0.25 mL, 1.827 mmol) at 0° C. and stirred for 30 min. After 30 min, $NaBH_4$ (69 mg, 1.827 mmol) was added at 0° C. and stirred at room temperature for 18 h. After cooling to 0° C., quenched with MeOH (2 mL) and heated to reflux for 6 h. The reaction mixture was diluted with EtOAc (20 mL), washed with water (20 mL), dried over anhydrous $Na_2SO_4$ and solvent was evaporated under reduced pressure. Crude compound was purified by column using 100-200 mesh silica gel. The column was eluted with 5% MeOH in DCM to afford 60 mg (yield: 41.66%) of the title compound as white solid.

$^1$H NMR (DMSO-$d_6$, 400 MHz, TMS) δ: 8.90 (1H, s), 8.278-8.273 (1H, d), 8.16-8.15 (1H, d), 7.66-7.62 (2H, m), 7.28-7.23 (1H, t), 7.09 (2H, s), 4.91-4.88 (1H, m), 3.57 (6H, br), 2.42 (4H, br), 1.58 (3H, s), 1.56 (3H, s).

LC-MS: m/z=397.1 (MH$^+$), $t_R$=0.33, method A.

20: [4-[6-amino-5-(1-isopropyltriazol-4-yl)-3-pyridyl]-2-methyl-phenyl]-morpholino-methanone

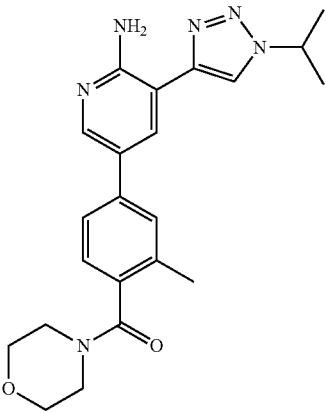 [SMILES: Cc1cc(-c2cnc(N)c(-c3cn(C(C)C)nn3)c2)ccc1C(=O)N1CCOCC1]

HATU (336 mg, 0.88 mmol) and DIPEA (0.30 mL, 1.77 mmol) were added to a solution of 4-(6-amino-5-(1-isopropyl-1H-1,2,3-triazol-4-yl)pyridin-3-yl)-2-methylbenzoic acid (200 mg, 0.59 mmol) in DMF (10.0 mL) at room temperature, after 5 min, morpholine (0.06 mL, 0.71 mmol) was

21: 3-(1-Isopropyltriazol-4-yl)-5-[3-methyl)phenyl]pyridin-2-amine

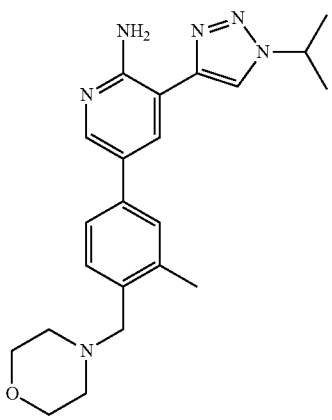

BF$_3$.Et$_2$O in THF (47-49%) (0.87 mL, 2.46 mmol) was added to a solution of [4-[6-amino-5-(1-isopropyltriazol-4-yl)-3-pyridyl]-2-methyl-phenyl]-morpholino-methanone (200 mg, 0.46 mmol) in THF (10.0 mL) at 0° C. The reaction mixture was stirred for 30 min, NaBH$_4$ (93.5 mg, 2.46 mmol) was added at 0° C., reaction mixture was slowly warmed to RT, stirred for 16 h. Reaction mixture was again cooled to 0° C., added MeOH (5.0 mL) and heated to 70° C. for 2 h. The reaction mixture was diluted with water (50 mL) and extracted with ethyl acetate (2×30 mL). Combined organic layers was dried over Na$_2$SO$_4$ and concentrated under reduced pressure. Crude product was purified by silica (100-200 mesh) column eluted with 2% MeOH in DCM. Product was further purified by Prep. HPLC furnished 30 mg (Yield: 15.5%) of the title compound as a white solid.

$^1$HNMR (DMSO-d$_6$, 400 MHz, TMS) δ: 8.91 (1H, s), 8.29-8.28 (1H, d), 8.17-8.16 (1H, d), 7.47 (1H, s), 8.44-8.42 (1H, d), 7.29-7.27 (1H, d), 7.04 (2H, br, s), 4.91-4.87 (1H, m), 3.57-3.55 (4H, t), 3.45 (2H, s), 2.40 (3H, s), 2.38-2.37 (4H, t), 1.58-1.56 (6H, d).

LC-MS: m/z=393.1 (MH$^+$), t$_R$=0.33, method A.

22: [4-[6-amino-5-(1-isopropyltriazol-4-yl)-3-pyridyl]-2-chloro-phenyl]-morpholino-methanone

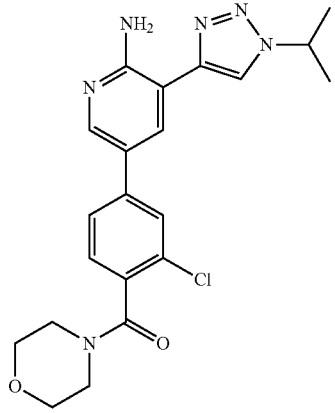

Cs$_2$CO$_3$ (682 mg, 2.10 mmol) was added to a solution of 5-bromo-3-(1-isopropyl-1H-[1,2,3]triazol-4-yl)-pyridin-2-ylamine (200 mg, 0.70 mmol) and (3-chloro-4-(morpholine-4-carbonyl)phenyl)boronic acid (229 mg, 0.85 mmol) in dioxane: water (7 mL: 3 mL) degassed the reaction mixture for 10 min with nitrogen. Then added Pd(PPh$_3$)$_4$ (40 mg, 0.035 mmol), degassed the reaction mixture for additional 10 min with nitrogen, the reaction mixture was heated to 120° C. in microwave for 1 h. The reaction mixture was diluted with water (50 mL) and extracted with ethyl acetate (3×30 mL). Combined organic layers was dried over Na$_2$SO$_4$ and concentrated under reduced pressure. Crude product was purified by silica (100-200 mesh) column eluted with 70-80% ethyl acetate in pet-ether to afford 68 mg (Yield: 22.5%) of the title compound as a pale yellow solid. Product was converted to its HCl salt by using HCl in ether (2M) to afford 60 mg of the HCl salt of the title compound as a pale yellow solid.

$^1$HNMR (DMSO-d$_6$, 400 MHz, TMS) δ: 9.17 (1H, s), 8.70 (1H, s), 8.50 (1H, d), 8.42-8.41 (2H, br), 7.99 (1H, d), 7.85-7.83 (1H, dd), 7.55-7.53 (1H, dd), 4.99-4.92 (1H, m), 3.71-3.64 (4H, br, s), 3.57-3.55 (2H, t), 3.18-3.16 (2H, t), 1.60-1.58 (6H, d).

LC-MS: m/z=427.4 (MH$^+$), t$_R$=0.44, method A.

23: 5-[3-Chloro-4-(morpholinomethyl)phenyl]-3-(1-isopropyltriazol-4-yl)pyridin-2-amine

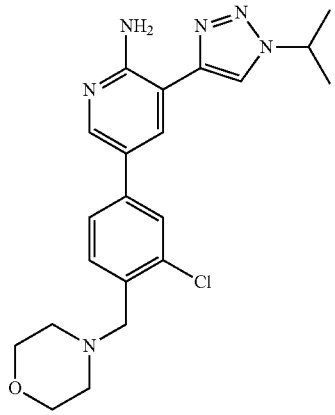

BH$_3$.DMS in THF (2M) (1.17 mL, 2.34 mmol) was added to a solution of [4-[6-amino-5-(1-isopropyltriazol-4-yl)-3- pyridyl]-2-chloro-phenyl]-morpholino-methanone (200 mg, 0.46 mmol) in THF (10.0 mL) at 0° C., then reaction mixture was heated to 70° C. for 4 h. Reaction mixture was cooled to 0° C., added MeOH (5.0 mL) to the reaction mixture, heated to 70° C. for 6 h. The reaction mixture was diluted with water (50 mL) and extracted with ethyl acetate (2×30 mL). Combined organic layers was dried over $Na_2SO_4$ and concentrated under reduced pressure. Crude product was purified by silica (100-200 mesh) column eluted with 2% MeOH in DCM to afford 131 mg (Yield: 67.7%) of the title compound as a white solid.

$^1$HNMR (DMSO-$d_6$, 400 MHz, TMS) δ: 8.94 (1H, s), 8.35-8.34 (1H, d), 8.22 (1H, d), 7.76 (1H, d), 7.66-7.64 (1H, dd), 7.54-7.52 (1H, d), 7.18 (2H, br, s), 4.93-4.86 (1H, m), 3.59 (6H, s), 2.44 (4H, s), 1.58-1.56 (6H, d).

LCMS Conditions:
Column: BEH C18 (2.1×50 mm) 1.7μ
M-Phase A: 5 mM Ammonium Acetate in $H_2O$
M-Phase B: ACN
T/% B: 0/03, 1.5/45, 2.5/45, 3.2/95, 4.7/95, 5/03
Flow: 0.4 ml/min
Diluent: MeOH
Purity: 95.01%
tR=2.90 min, m/z=413.2[M+H]$^+$ 24: 3-(1-Isopropyltriazol-4-yl)-5-[3-(morpholinomethyl)phenyl]pyridin-2-amine

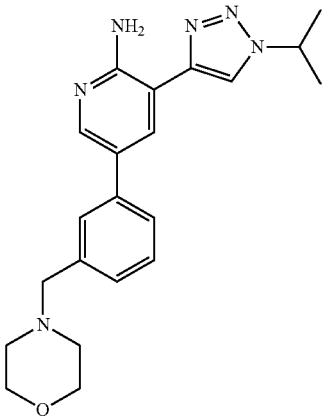 [SMILES: CC(C)n1cc(-c2cc(-c3cccc(CN4CCOCC4)c3)cnc2N)nn1]

$Cs_2CO_3$ (858 mg, 2.64 mmol) was added to a solution of (3-(morpholinomethyl)phenyl)boronic acid (250 mg, 0.88 mmol) and 5-bromo-3-(1-isopropyl-1H-[1,2,3]triazol-4-yl)-pyridin-2-ylamine (215 mg, 0.97 mmol) in dioxane: water (8 mL: 4 mL) degassed the reaction mixture for 10 min with nitrogen. Then added Pd(PPh$_3$)$_4$ (50 mg, 0.044 mmol), degassed the reaction mixture for additional 10 min with nitrogen, the reaction mixture was heated to 120° C. in microwave for 1 h. The reaction mixture was diluted with water (50 mL) and extracted with ethyl acetate (2×30 mL). Combined organic layers was dried over $Na_2SO_4$ and concentrated under reduced pressure. Crude product was purified by silica (100-200 mesh) column eluted with 80-90% ethyl acetate in pet-ether to afford 195 mg (Yield: 58.13%) of the title compound as a pale yellow solid. Product was converted to its HCl salt by using HCl in ether (2M) to afford 202 mg as a pale yellow solid.

$^1$HNMR (DMSO-$d_6$, 400 MHz, TMS) δ: 11.60 (1H, br, s), 9.51 (1H, s), 9.04 (1H, s), 8.54 (3H, br, s), 8.37 (1H, s), 7.89-7.88 (1H, d), 7.60-7.52 (2H, m), 4.99-4.92 (1H, m), 4.44 (2H, s), 3.93 (4H, s), 3.23 (2H, s), 3.16 (2H, br, s), 1.60-1.58 (6H, d).

LC-MS: m/z=379.5 (MH$^+$), $t_R$=0.36, method A.

25: [3-[6-Amino-5-(1-isopropyltriazol-4-yl)-3-pyridyl]phenyl]-morpholino-methanone

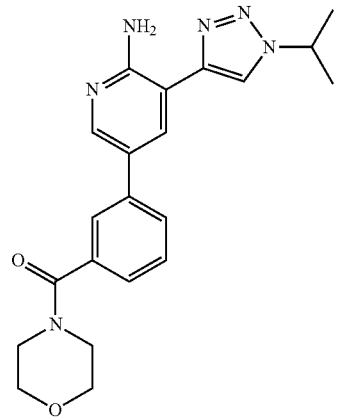 [SMILES: CC(C)n1cc(-c2cc(-c3cccc(C(=O)N4CCOCC4)c3)cnc2N)nn1]

$Cs_2CO_3$ (858 mg, 2.64 mmol) was added to a solution of 5-bromo-3-(1-isopropyl-1H-[1,2,3]triazol-4-yl)-pyridin-2-ylamine (250 mg, 0.88 mmol) and (3-(morpholine-4-carbonyl)phenyl)boronic acid (228 mg, 0.97 mmol) in dioxane: water (8 mL: 4 mL) degassed the reaction mixture for 10 min with nitrogen. Then added Pd(PPh$_3$)$_4$ (50 mg, 0.044 mmol), degassed the reaction mixture for additional 10 min with nitrogen, the reaction mixture was heated to 120° C. in microwave for 1 h. After completion of reaction, the reaction mixture was diluted with water (50 mL) and extracted with ethyl acetate (2×30 mL). Combined organic layers was dried over $Na_2SO_4$ and concentrated under reduced pressure. Crude product was purified by silica (100-200 mesh) column eluted with 80-90% ethyl acetate in pet-ether to afford 210 mg (Yield: 60.34%) of the title compound as a pale yellow solid. Product was converted to its HCl salt by using HCl in ether (2M) to afford 208 mg as an off-white solid.

$^1$HNMR (DMSO-$d_6$, 400 MHz, TMS) δ: 9.21 (1H, s), 8.73 (1H, s), 8.48 (3H, br, s), 7.89-7.87 (1H, d), 7.82 (1H, s), 7.61-7.57 (1H, t), 7.46-7.44 (1H, d), 4.99-4.92 (1H, m), 3.66-3.59 (8H, br), 1.59-1.58 (6H, d).

LC-MS: m/z=393.5 (MH$^+$), $t_R$=0.41, method A.

26: [3-[6-Amino-5-(1-isopropyltriazol-4-yl)-3-pyridyl]-5-chloro-phenyl]-morpholino-methanone

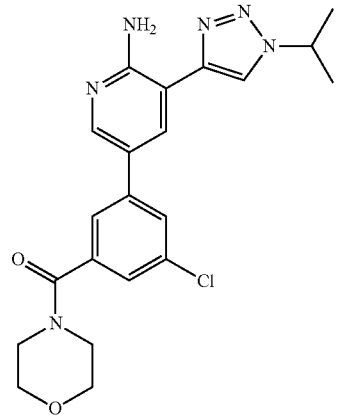 [SMILES: CC(C)n1cc(-c2cc(-c3cc(Cl)cc(C(=O)N4CCOCC4)c3)cnc2N)nn1]

Cs₂CO₃ (682 mg, 2.10 mmol) was added to a solution of 5-bromo-3-(1-isopropyl-1H-[1,2,3]triazol-4-yl)-pyridin-2-ylamine (200 mg, 0.70 mmol) and (3-chloro-5-(morpholine-4-carbonyl)phenyl)boronic acid (210 mg, 0.78 mmol) in dioxane: water (8 mL: 4 mL) degassed the reaction mixture for 10 min with nitrogen. Then added Pd(PPh₃)₄ (40 mg, 0.035 mmol), degassed the reaction mixture for additional 10 min with nitrogen, the reaction mixture was heated to 120° C. in microwave for 1 h. The reaction mixture was diluted with water (50 mL) and extracted with ethyl acetate (2×30 mL). Combined organic layers was dried over Na₂SO₄ and concentrated under reduced pressure. Crude product was purified by silica (100-200 mesh) column eluted with 80-90% ethyl acetate in pet-ether to afford 46 mg (Yield: 47.0%) of the title compound as a pale yellow solid.

¹HNMR (DMSO-d₆, 400 MHz, TMS) δ: 8.96 (1H, s), 8.41-8.40 (1H, d), 8.26-8.25 (1H, d), 7.87 (1H, s), 7.68 (1H, s), 7.38 (1H, s), 7.28 (2H, s), 4.94-4.87 (1H, m), 3.64-3.57 (6H, br), 3.36 (2H, br), 1.58-1.57 (6H, d).

LC-MS: m/z=427.4 (MH⁺), t_R=0.48, method A.

27: 5-[3-Chloro-5-(morpholinomethyl)phenyl]-3-(1-isopropyltriazol-4-yl)pyridin-2-amine

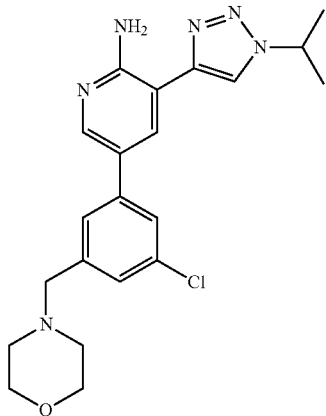 [SMILES: CC(C)n1cc(-c2cc(-c3cc(Cl)cc(CN4CCOCC4)c3)cnc2N)nn1]

BF₃.Et₂O in THF (47-49%) (0.70 mL, 2.34 mmol) was added to a solution of [3-[6-amino-5-(1-isopropyltriazol-4-yl)-3-pyridyl]-5-chloro-phenyl]-morpholino-methanone (200 mg, 0.46 mmol) in THF (10.0 mL) at 0° C., then reaction mixture was stirred for 30 min, added NaBH₄ (89 mg, 2.36 mmol) at 0° C., reaction mixture was slowly warmed to RT, stirred for 16 h. Reaction mixture was cooled to 0° C., added MeOH (5.0 mL) to the reaction mixture, heated to 70° C. for 2 h. The reaction mixture was diluted with water (50 mL) and extracted with ethyl acetate (2×30 mL). Combined organic layers was dried over Na₂SO₄ and concentrated under reduced pressure. Crude product was purified by silica (100-200 mesh) column eluted with 2% MeOH in DCM to afford 39 mg (Yield: 20.2%) of the title compound. This was converted to its HCl salt by using HCl in ether (2M) to afford 45 mg as a pale gray solid.

¹HNMR (D₂O, 400 MHz, TMS) δ: 8.63 (1H, s), 8.46-8.45 (1H, d), 8.18 (1H, d), 7.83 (1H, s), 7.68 (1H, s), 7.63 (1H, s), 5.03-4.96 (1H, m), 4.45 (2H, s), 4.15-3.82 (4H, br), 3.41 (4H, br), 1.65-1.64 (6H, d).

LC-MS: m/z=413.1 (MH⁺), t_R=0.4, method A.

28: [4-[6-Amino-5-(1-isopropyltriazol-4-yl)-3-pyridyl]phenyl]-morpholino-methanone

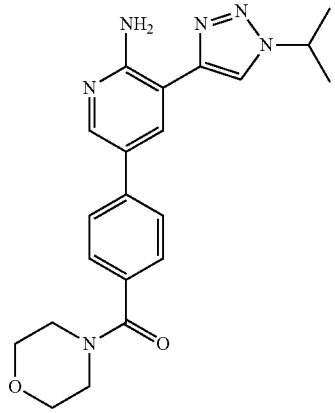 [SMILES: CC(C)n1cc(-c2cc(-c3ccc(C(=O)N4CCOCC4)cc3)cnc2N)nn1]

To a solution of 5-bromo-3-(1-isopropyl-1H-[1,2,3]triazol-4-yl)-pyridin-2-ylamine (200 mg, 0.70 mmol) and (4-(morpholine-4-carbonyl)phenyl)boronic acid (183 mg, 0.77 mmol) in 1,4-dioxane (10.0 mL)/water (5.0 mL) was added Cs₂CO₃ (690 mg, 2.12 mmol) at room temperature. The reaction mixture was degassed with argon for 30 min. Then Pd(PPh₃)₄ (40 mg, 0.03 mmol) was added and allowed to stir at 110° C. for 30 min in CEM micro wave. The reaction mixture was cooled to RT, diluted with EtOAc (50 mL) and washed with water (50 mL). The organic layer was washed with brine solution (20 mL), dried over anhydrous Na₂SO₄ and solvent was evaporated under reduced pressure to afford crude compound. Crude compound was purified by column using 100-200 mesh silica gel. The column was eluted with 5% MeOH in DCM to afford 100 mg (yield: 35.97%) of the title compound as pale yellow solid.

¹H NMR (DMSO-d₆, 400 MHz, TMS) δ: 8.95 (1H, s), 8.378-8.373 (1H, d), 8.266-8.261 (1H, d), 7.78-7.76 (2H, d), 7.49-7.47 (2H, d), 7.18 (2H, s), 4.93-4.87 (1H, m), 3.61 (8H, br), 1.58 (3H, s), 1.56 (3H, s).

LC-MS: m/z=393.5 (MH⁺), t_R=0.4, method A.

29: 3-(5-cyclopropyl-1,3,4-oxadiazol-2-yl)-5-[3-(morpholinomethyl)phenyl]pyridin-2-amine

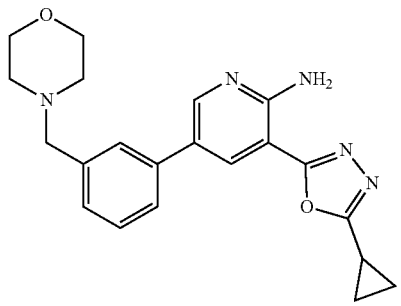 [SMILES: Nc1ncc(-c2cccc(CN3CCOCC3)c2)cc1-c1nnc(C2CC2)o1]

To a solution of 5-bromo-3-(5-cyclopropyl-[1,3,4]oxadiazol-2-yl)-pyridin-2-ylamine (400 mg, 1.42 mmol) in dioxane (10 mL) and water (6 mL) were added K₂CO₃ (587 mg; 4.26 mmol), (3-(morpholinomethyl)phenyl)boronic acid (348 mg; 1.56 mmol) in a sealed tube. The reaction mixture was degassed with argon for 30 min, then added Pd(PPh$_3$)$_4$ (82.0 mg; 0.07 mmol) to the reaction mixture. The reaction mixture was stirred for 18 h at 100° C. The reaction mixture was diluted with water (50 mL) extracted with ethyl acetate (2×50 mL) and organic layer was washed with brine, dried over anhydrous sodium sulphate and concentrated under reduced pressure. Crude compound was purified by column chromatography using 100-200 mesh silica gel and eluted with 100% ethyl acetate, which is further purified by washing with 30% chloroform in hexane to afford 90 mg (Yield: 16.7%) of the title compound, as a yellow colour solid.

$^1$HNMR (DMSO-d$_6$, 400 MHz, TMS) δ: 8.52-8.51 (1H, d), 8.20-8.19 (1H, d), 7.58-7.54 (2H, m), 7.43-7.39 (1H, t), 7.35 (2H, s), 7.31-7.28 (1H, d), 3.59-3.54 (6H, m), 2.40-2.30 (5H, m), 1.20-1.15 (4H, m).

LCMS Conditions:
Column: BEH C 18 (2.1×50 mm) 1.7µ
M-Phase A: 5 mM NH$_4$OAC in H$_2$0
M-Phase B: ACN
T/% B: 0/03, 1.5/45, 2.5/45, 3.2/95, 4.7/95, 5/03
Flow: 0.4 ml/min
Diluent: MeOH
Drift Tube Temp: 55° C.
Gas Pressure: 30 psi
Nebulizer Temp: 65%
Gain: 500
Purity: 97.21%
tR=2.10 min, m/z=378.2[M+H]$^+$ 30: 2-[4-[6-amino-5-(1-isopropyltriazol-4-yl)-3-pyridyl]phenyl]-1-morpholino-ethanone

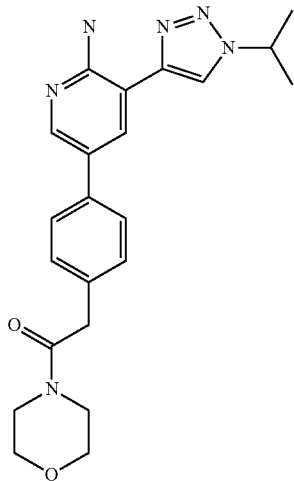 [SMILES: CC(C)n1cc(-c2cc(-c3ccc(CC(=O)N4CCOCC4)cc3)cnc2N)nn1]

To a solution of 1-Morpholin-4-yl-2-[4-(4,4,5,5-tetramethyl-[1,3,2]dioxaborolan-2-yl)-phenyl]-ethanone (129 mg, 0.39 mmol) and 5-bromo-3-(1-isopropyl-1H-[1,2,3]triazol-4-yl)-pyridin-2-ylamine (100 mg, 0.35 mmol) in 1,4-dioxane (6.0 mL)/water (4.0 mL) was added Cs$_2$CO$_3$ (284 mg, 0.87 mmol) at room temperature. N$_2$ was purged through the reaction mixture for 10 min. Pd(PPh$_3$)$_4$ (20 mg, 0.017 mmol) was added and through the reaction mixture N$_2$ was purged for 10 min and stirred at 100° C. for 16 h. The reaction mixture was cooled to RT, diluted with EtOAc (50 mL) and washed with water (50 mL). The organic layer was washed with brine solution (50 mL), dried over anhydrous Na$_2$SO$_4$ and solvent was evaporated under reduced pressure. Crude compound was purified by column chromatography using 100-200 mesh silica gel and eluted with 2-3% MeOH in DCM to afford 40 mg (yield: 27.7%) of the title compound as brown semisolid. Product was converted to its HCl salt by using 2M HCl in ether to afford 42 mg of an off-white solid.

$^1$H NMR (DMSO-d6, 400 MHz, TMS) δ: 9.20 (1H, s), 8.71-8.70 (1H, d), 8.40-8.39 (1H, d), 7.73-7.71 (2H, d), 7.38-7.36 (2H, d), 4.99-4.92 (1H, m), 3.79 (2H, s), 3.56-3.45 (8H, m), 1.59-1.58 (6H, d).

LC-MS: m/z=407.1 (MH$^+$), t$_R$=0.42, method A.

LRRK2 Wild-Type and G2019S Kinase Activity Assay.

LRRK2 kinase activity is measured using a LanthaScreen kinase activity assay available from Invitrogen (Life Technologies Corporation). The assay is a homogeneous time resolved-fluorescence resonance energy transfer (TR-FRET) assay that measures phosphorylation of a fluorescein-labelled peptide substrate (flouorescein-LRRKtide, Fluorescein-GAGRLGRDKYKTLRQIRQ) (SEQ ID NO 1) as a result of LRRK2 kinase activity. The phosphorylated peptide is recognized by a terbium-labelled phospho-specific anti-LRRKtide antibody and, subsequently, the phosphorylated LRRKtide can be quantified by the extent of TR-FRET between the terbium donor and fluorescein acceptor.

The LRRK2 kinase is obtained from Invitrogen (Life Technologies Corporation) and comprises residue 970 to 2527 of the full length human wildtype LRRK2 kinase or a similar sequence with the G2019S mutation. As discussed above, this mutation increases the kinase activity relative to the wild type. The kinase reactions are performed in a 20 L volume in 384-well plates. The kinase reaction buffer consists of 50 mM Tris pH 8.5, 0.01% BRIJ-35, 10 mM MgCl2, 1 mM EGTA, and 2 mM DTT.

In the assay, 1 nM LRRK2 WT or 250 pM LRRK2 G2019S kinase is incubated with the test compound (typically at 0 to 30 µM) for 30 minutes before the kinase reaction is initiated by addition of 1.3 mM ATP and 0.4 µM fluorescein-LRRKtide. The reaction mixture (20 µl total volume) is incubated for 2 hours at 30° C. before the reaction is terminated by addition of 10 mM EDTA and 1 nM terbium-labelled anti-phospho-LRRKtide antibody (final volume 20 µl). The mixture is further incubated for 30 minutes at RT. TR-FRET is measured by excitation of the terbium-donor with 340 nm light and subsequent (delay time 100 µs) measurement of terbium and fluorescein emission at 495 nm and 520 nm, respectively, over a time window of 1000 µs. The measurement is repeated 10 times for fluorescein and 10 times for terbium emission with a 2000 µs time window between repeats. TR-FRET measurements are performed on a Biomek Synergy plate. The TR-FRET signal is calculated as the emission-ratio at 520 nm over 495 nm.

The TR-FRET ratio readout for test compounds is normalized to 0% inhibition corresponding to TR-FRET ratio measured in control wells with no inhibition of the kinase activity and 100% inhibition corresponding to TR-FRET ratio measured in control wells with no kinase. Test compound potency (IC50) was estimated by nonlinear regression using the sigmoidal dose-response (variable slope) using Xlfit 4 (IDBS, Guildford, Surrey, UK, model 205).

$$y=(A+((B-A)/(1+((C/x)^D))))$$

where y is the normalized TR-TRET ratio measurement for a given concentration of test compound, x is the concentration of test compound, A is the estimated efficacy (% inhibition) at infinite compound dilution, and B is the maximal efficacy (% inhibition). C is the IC50 value and D is the Hill slope coefficient. IC$_{50}$ estimates were obtained from independent experiment and the logarithmic average was calculated.

The table below shows the IC$_{50}$ values in nM obtained as described above for the exemplified compounds

| Example no: | LRRK2 G2019S IC50 (nM) | LRRK2 WT IC50 (nM) |
|---|---|---|
| 1 | 910 | |
| 2 | 1000 | 570 |
| 3 | 710 | 970 |
| 4 | 860 | 3600 |
| 5 | 380 | 2200 |
| 6 | 390 | 490 |
| 7 | 1000 | 3300 |
| 8 | 880 | 2200 |
| 9 | 540 | 550 |
| 10 | 350 | 620 |
| 11 | 340 | 570 |
| 12 | 160 | 300 |
| 13 | 280 | 340 |
| 14 | 340 | 600 |
| 15 | 370 | 200 |
| 16 | 510 | 580 |
| 17 | 95 | 91 |
| 18 | 86 | 93 |
| 19 | 880 | 1000 |
| 20 | 110 | 99 |
| 21 | 240 | 260 |
| 22 | 290 | 290 |
| 23 | 220 | 320 |
| 24 | 500 | 370 |
| 25 | 950 | 650 |
| 26 | 690 | 490 |
| 27 | 760 | 610 |
| 28 | 430 | 370 |
| 29 | 760 | 900 |
| 30 | 520 | 670 |

The invention claimed is:

1. A compound of Formula A:

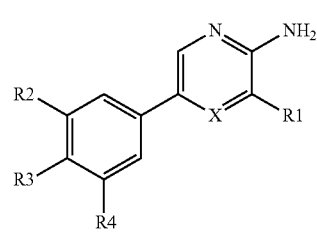

[A]

wherein
R1 represents triazolyl or oxadiazolyl, said triazolyl or oxadizolyl may optionally be substituted with 1 R5 group,
X represents N or CH when R1 represents triazolyl or when R1 represents oxadiazolyl X represents CH,
R5 represents $C_1$-$C_6$ alkyl, $C_3$-$C_6$ cycloalkyl or a 5-6 membered heterocyclic ring with 1 or 2 heteroatom(s), said cycloalkyl or heterocyclic ring are optionally substituted with 1 or 2 $C_1$-$C_3$ alkyl or 1 or 2 $C_1$-$C_3$ alkoxy,
R2, R3 and R4 each independently represents hydrogen, halogen, $C_1$-$C_6$ alkyl, $C_1$-$C_6$ alkoxy, $O(CH_2)_nCF_3$, $(CH_2)_nR6$, $(C=O)R6$ or $(CH_2)_n(C=O)R6$, n=0, 1, 2 or 3, or
R2 and R3 or R3 and R4 may together with the atom they are attached to form a 9-10 membered bicyclic heterocyclic ring with 1 or 2 heteroatom(s), said bicyclic heterocyclic ring may optionally be substituted 1 or 2 $C_1$-$C_6$ alkyl or 1 or 2 $C_1$-$C_6$ alkoxy,
R6 represents a 5-6 membered heterocyclic ring with 1, 2 or 3 heteroatom(s), said heterocyclic ring may optionally be substituted with 1 or 2 $C_1$-$C_3$ alkyl or 1 or 2 $C_1$-$C_3$ alkoxy,
or a pharmaceutically acceptable salt thereof.

2. The compound according to claim 1, wherein the heteroatom(s) are independently selected from N, O or S.

3. The compound according to claim 1, wherein the halogen(s) are independently fluoro, chloro, bromo or iodo.

4. The compound according to claim 1, wherein said $C_1$-$C_6$ alkyl group is methyl, ethyl, propyl, isopropyl, butyl, isobutyl, t-butyl, pentyl or isopentyl.

5. The compound according to claim 1, wherein said $C_1$-$C_3$ alkyl group is methyl, ethyl, propyl, or isopropyl.

6. The compound according to claim 1, wherein the $C_1$-$C_6$ alkoxy group is methoxy, ethoxy, propoxy, butoxy, isobutoxy, t-butoxy, pentoxy, or isopropoxy.

7. The compound according to claim 1, wherein the $C_1$-$C_3$ alkoxy group is methoxy, ethoxy, propoxy or isopropoxy.

8. The compound according to claim 1, wherein R1 is:

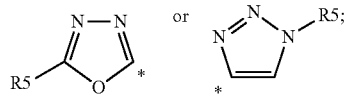

wherein * denotes the attachment point.

9. The compound according to claim 1, wherein R5 is selected from the group consisting of $C_1$-$C_3$ alkyl, $C_3$-$C_6$ cycloalkyl,

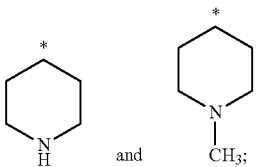

wherein * denotes the attachment point.

10. The compound according to claim 1, wherein R2, R3 and/or R4 is selected from the group consisting of:

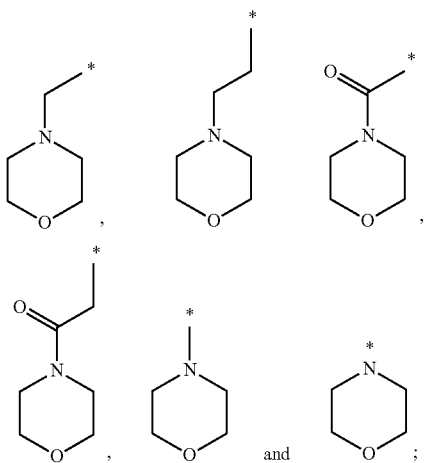

wherein * denotes the attachment point.

11. The compound according to claim 1, wherein R2 and R3 or R3 and R4 together with the atom they are attached to form a bicyclic heterocyclic ring selected from the group consisting of:

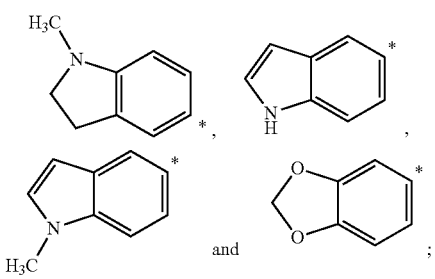

wherein * denotes the attachment point.

12. The compound according to claim 1 wherein the compound is selected from the group consisting of:
(1) 5-(1H-Indol-5-yl)-3-(5-isopropyl-[1,3,4]oxadiazol-2-yl)-pyridin-2-ylamine,
(2) 3-(5-Cyclopropyl-[1,3,4]oxadiazol-2-yl)-5-(1H-indol-5-yl)-pyridin-2-ylamine,
(3) 3-(5-Cyclopropyl-[1,3,4]oxadiazol-2-yl)-5-(1-methyl-2,3-dihydro-1H-indol-5-yl)-pyridin-2-ylamine,
(4) 3-[5-(1-Methyl-piperidin-4-yl)-[1,3,4]oxadiazol-2-yl]-5-p-tolyl-pyridin-2-ylamine,
(5) 5-(1-Methyl-2,3-dihydro-1H-indol-5-yl)-3-(5-piperidin-4-yl-[1,3,4]oxadiazol-2-yl)-pyridin-2-ylamine,
(6) 3-(5-Cyclopropyl-[1,3,4]oxadiazol-2-yl)-5-(4-morpholin-4-ylmethyl-phenyl)-pyridin-2-ylamine,
(7) 5-(3-Methoxy-phenyl)-3-(5-piperidin-4-yl-[1,3,4]oxadiazol-2-yl)-pyridin-2-ylamine,
(8) 5-(3-Methoxy-phenyl)-3-[5-(1-methyl-piperidin-4-yl)-[1,3,4]oxadiazol-2-yl]-pyridin-2-ylamine,
(9) 3-(1-Isopropyl-1H-[1,2,3]triazol-4-yl)-5-(1-methyl-1H-indol-5-yl)-pyridin-2-ylamine,
(10) 3-(1-Isopropyl-1H-[1,2,3]triazol-4-yl)-5-(1-methyl-2,3-dihydro-1H-indol-5-yl)-pyridin-2-ylamine,
(11) 3-(1-Isopropyl-1H-[1,2,3]triazol-4-yl)-5-(1-methyl-2,3-dihydro-1H-indol-5-yl)-pyrazin-2-ylamine,
(12) 3-(1-Isopropyl-1H-[1,2,3]triazol-4-yl)-5-(4-morpholin-4-ylmethyl-phenyl)-pyridin-2-ylamine,
(13) 3-(1-Isopropyl-1H-[1,2,3]triazol-4-yl)-5-(4-morpholin-4-yl-phenyl)-pyridin-2-ylamine,
(14) 3-(1-Isopropyl-1H-[1,2,3]triazol-4-yl)-5-[4-(2-morpholin-4-yl-ethyl)-phenyl]-pyridin-2-ylamine,
(15) 5-(3-fluoro-4-(morpholinomethyl)phenyl)-3-(1-isopropyl-1H-1,2,3-triazol-4-yl)pyridin-2-amine,
(16) (4-(6-amino-5-(1-isopropyl-1H-1,2,3-triazol-4-yl)pyridin-3-yl)-2-fluorophenyl)(morpholino)methanone,
(17) [4-[6-amino-5-(1-isopropyltriazol-4-yl)-3-pyridyl]-2-methoxy-phenyl]-morpholino-methanone,
(18) 3-(1-isopropyltriazol-4-yl)-5-[3-methoxy-4-(morpholinomethyl)phenyl]pyridin-2-amine,
(19) 5-[4-fluoro-3-(morpholinomethyl)phenyl]-3-(1-isopropyltriazol-4-yl)pyridin-2-amine,
(20) [4-[6-amino-5-(1-isopropyltriazol-4-yl)-3-pyridyl]-2-methyl-phenyl]-morpholino-methanone,
(21) 3-(1-Isopropyltriazol-4-yl)-5-[3-methyl-4-(morpholinomethyl)phenyl]pyridin-2-amine,
(22) [4-[6-amino-5-(1-isopropyltriazol-4-yl)-3-pyridyl]-2-chloro-phenyl]-morpholino-methanone,
(23) 5-[3-Chloro-4-(morpholinomethyl)phenyl]-3-(1-isopropyltriazol-4-yl)pyridin-2-amine,
(24) 3-(1-Isopropyltriazol-4-yl)-5-[3-(morpholinomethyl)phenyl]pyridin-2-amine,
(25) [3-[6-Amino-5-(1-isopropyltriazol-4-yl)-3-pyridyl]phenyl]-morpholino-methanone,
(26) [3-[6-Amino-5-(1-isopropyltriazol-4-yl)-3-pyridyl]-5-chloro-phenyl]-morpholino-methanone,
(27) 5-[3-Chloro-5-(morpholinomethyl)phenyl]-3-(1-isopropyltriazol-4-yl)pyridin-2-amine,
(28) [4-[6-Amino-5-(1-isopropyltriazol-4-yl)-3-pyridyl]phenyl]-morpholino-methanone,
(29) 3-(5-cyclopropyl-1,3,4-oxadiazol-2-yl)-5-[3-(morpholinomethyl)phenyl]pyridin-2-amine,
(30) 2-[4-[6-amino-5-(1-isopropyltriazol-4-yl)-3-pyridyl]phenyl]-1-morpholino-ethanone,
or a pharmaceutically acceptable salt thereof.

13. A pharmaceutical composition comprising a compound according to claim 1 and one or more pharmaceutically acceptable carriers or diluents.

14. A method of treating a disease or disorder characterised by over-expression of LRRK2 or a mutated form of LRRK2 comprising administering a therapeutically effective amount of a compound according to claim 1 to a subject in need thereof, wherein the mutated form of LRRK2 is G2019S, I2020T, M1646T, G2385R or A419V.

15. The method of claim 14, wherein the disease or disorder is Lewy body dementia or Parkinson's disease.

16. The method according to claim 15 wherein the Parkinson's disease is idiopathic Parkinson's disease, sporadic Parkinson's disease or Parkinson's disease in patient carrying a G2019S mutation in LRRK2.

17. A method of treating cancer or an immune related disorder comprising administering a therapeutically effective amount of a compound according to claim 1 to a subject in need thereof, wherein the cancer or immune related disorder is characterised by over-expression of LRRK2 or a mutated form of LRRK2, and wherein the mutated form of LRRK2 is G2019S, I2020T, M1646T, G2385R or A419V.

18. The method according to claim 17 wherein the cancer is in the brain, lungs, kidney, spleen or blood organs of the subject.

19. The method according to claim 17 wherein the cancer or immune related disorder is selected from the group consisting of renal cancer, lung cancer, skin cancer, papillary renal carcinoma, thyroid carcinoma, Chron's disease, ulcerative colitis and leprosy.

\* \* \* \* \*